US012678064B2

(12) United States Patent
Su et al.

(10) Patent No.: US 12,678,064 B2
(45) Date of Patent: Jul. 14, 2026

(54) BLOOD PRESSURE MEASUREMENT METHOD FOR WEARABLE DEVICE AND WEARABLE DEVICE

(71) Applicant: Honor Device Co., Ltd., Shenzhen (CN)

(72) Inventors: Dan Su, Shenzhen (CN); Yi Liu, Shenzhen (CN); Zhibo Xie, Shenzhen (CN); Hao Chong, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 5 days.

(21) Appl. No.: 18/855,750

(22) PCT Filed: Apr. 10, 2023

(86) PCT No.: PCT/CN2023/087375
§ 371 (c)(1),
(2) Date: Oct. 10, 2024

(87) PCT Pub. No.: WO2024/021680
PCT Pub. Date: Feb. 1, 2024

(65) Prior Publication Data
US 2025/0241549 A1 Jul. 31, 2025

(30) Foreign Application Priority Data
Jul. 25, 2022 (CN) .......................... 202210875925.5

(51) Int. Cl.
| A61B 5/024 | (2006.01) |
| A61B 5/00 | (2006.01) |
| A61B 5/022 | (2006.01) |

(52) U.S. Cl.
CPC ...... A61B 5/02422 (2013.01); A61B 5/02233 (2013.01); A61B 5/6843 (2013.01);
(Continued)

(58) Field of Classification Search
CPC ............ A61B 5/02422; A61B 5/02233; A61B 5/6843; A61B 5/7264; A61B 5/743;
(Continued)

(56) References Cited

U.S. PATENT DOCUMENTS

| 10,874,348 B1 | 12/2020 | Han et al. |
| 2014/0273858 A1* | 9/2014 | Panther .............. A61B 5/02438 |
| | | 455/41.2 |

(Continued)

FOREIGN PATENT DOCUMENTS

| CN | 110141197 A | 8/2019 |
| CN | 111107891 A | 5/2020 |

(Continued)

*Primary Examiner* — Oommen Jacob
(74) *Attorney, Agent, or Firm* — Leydig, Voit & Mayer, Ltd.

(57) ABSTRACT

This application provides a blood pressure measurement method for a wearable device and a wearable device, so as to improve measurement accuracy of a blood pressure value. The wearable device includes a pressure transducer (PT) and a photoplethysmography (PPG) module. The PT and the PPG module are deployed at a target position of the wearable device. The target position includes a position for contacting a wearer when the wearable device is in a worn state. The method includes: obtaining a pressure value collected by the PT; obtaining a PPG signal collected by the PPG module; and determining a blood pressure value of the wearer based on the pressure value and the PPG signal.

14 Claims, 14 Drawing Sheets

(52) U.S. Cl.
CPC ............ *A61B 5/7264* (2013.01); *A61B 5/743* (2013.01); *A61B 2562/0219* (2013.01)

(58) Field of Classification Search
CPC ........ A61B 2562/0219; A61B 5/02225; A61B 5/02241; A61B 5/486; A61B 5/6898; A61B 5/7221; A61B 5/7425; A61B 5/02116; A61B 5/681; A61B 5/7267; A61B 5/02108; A61B 5/0295

See application file for complete search history.

(56) References Cited

U.S. PATENT DOCUMENTS

| | | | |
|---|---|---|---|
| 2016/0029943 A1* | 2/2016 | Mizuochi ............. | A61B 5/0022 600/595 |
| 2017/0095168 A1* | 4/2017 | Kwon ................ | A61B 5/02125 |
| 2017/0251935 A1 | 9/2017 | Yuen | |
| 2018/0184920 A1 | 7/2018 | Rabinovich et al. | |
| 2019/0008399 A1 | 1/2019 | Mukkamala et al. | |
| 2019/0313979 A1* | 10/2019 | Kang ................ | A61B 5/02433 |
| 2020/0113442 A1* | 4/2020 | Yuan .................... | A61B 5/0022 |
| 2020/0146568 A1 | 5/2020 | Park et al. | |
| 2020/0215246 A1 | 7/2020 | Tal et al. | |
| 2020/0321793 A1* | 10/2020 | Al-Ali ................. | A61B 5/0235 |
| 2021/0022677 A1* | 1/2021 | Kang ................... | A61B 5/0205 |
| 2021/0353164 A1* | 11/2021 | Chegani .............. | A61B 5/0245 |
| 2022/0175261 A1* | 6/2022 | Li ........................ | A61B 5/6826 |
| 2023/0040540 A1* | 2/2023 | Lange ................... | A61B 5/022 |
| 2023/0200668 A1* | 6/2023 | Reynolds ............. | A61B 5/6898 600/490 |
| 2025/0241549 A1* | 7/2025 | Su ........................ | A61B 5/6898 |

FOREIGN PATENT DOCUMENTS

| | | |
|---|---|---|
| CN | 113080913 A | 7/2021 |
| EP | 3360469 A1 | 8/2018 |
| WO | 2021190377 A1 | 9/2021 |
| WO | 2023284727 A1 | 1/2023 |
| WO | 2023031906 A1 | 3/2023 |

\* cited by examiner

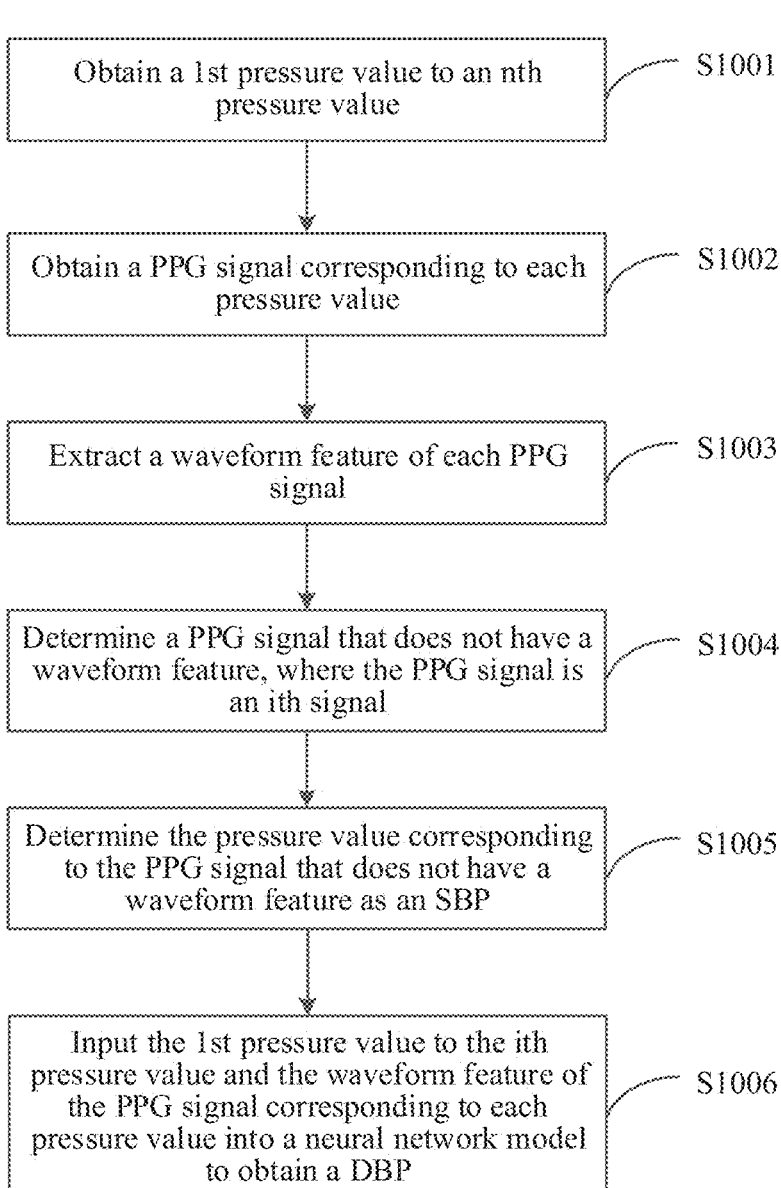

1000

Obtain a 1st pressure value to an nth pressure value — S1001

Obtain a PPG signal corresponding to each pressure value — S1002

Extract a waveform feature of each PPG signal — S1003

Determine a PPG signal that does not have a waveform feature, where the PPG signal is an ith signal — S1004

Determine the pressure value corresponding to the PPG signal that does not have a waveform feature as an SBP — S1005

Input the 1st pressure value to the ith pressure value and the waveform feature of the PPG signal corresponding to each pressure value into a neural network model to obtain a DBP — S1006

FIG. 10

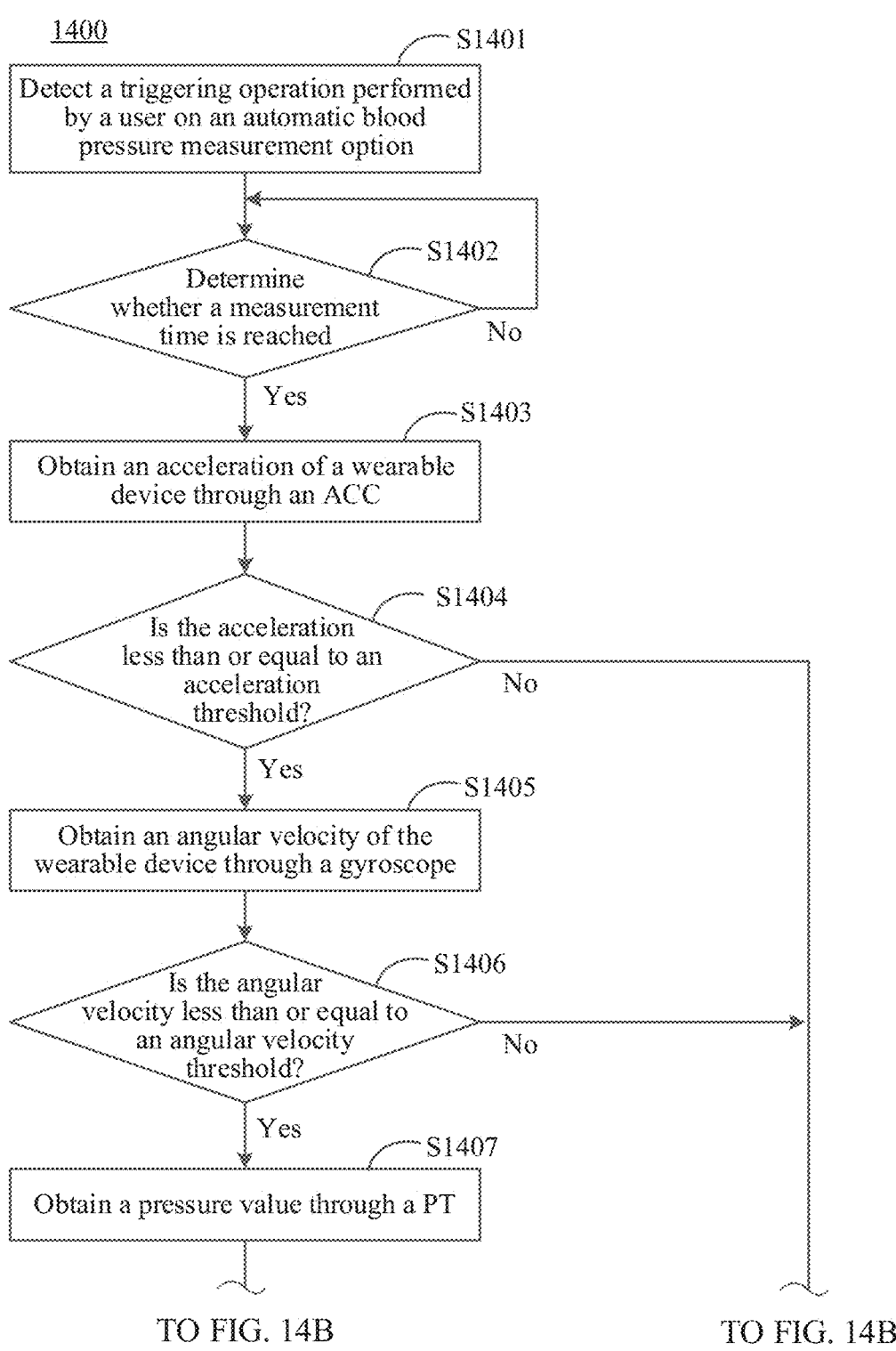

<u>1400</u>

S1401

Detect a triggering operation performed by a user on an automatic blood pressure measurement option

S1402

Determine whether a measurement time is reached

No

Yes

S1403

Obtain an acceleration of a wearable device through an ACC

S1404

Is the acceleration less than or equal to an acceleration threshold?

No

Yes

S1405

Obtain an angular velocity of the wearable device through a gyroscope

S1406

Is the angular velocity less than or equal to an angular velocity threshold?

No

Yes

S1407

Obtain a pressure value through a PT

BLOOD PRESSURE MEASUREMENT METHOD FOR WEARABLE DEVICE AND WEARABLE DEVICE

CROSS-REFERENCE TO RELATED APPLICATIONS

This application is a national stage of International Application No. PCT/CN2023/087375, filed on Apr. 10, 2023, which claims priority to Chinese Patent Application No. 202210875925.5, filed on Jul. 25, 2022. The disclosures of both of the aforementioned applications are hereby incorporated by reference in their entireties.

TECHNICAL FIELD

This application relates to the field of terminal technologies, and in particular, to a blood pressure measurement method for a wearable device and a wearable device.

BACKGROUND

With the development of wearable devices, the wearable device may support increasingly more functions. To satisfy needs of users for health management thereof, a relatively large quantity of wearable devices may support a human body data monitoring function of the user. For example, a smartwatch may measure a human body feature such as a heart rate, a respiration rate, blood pressure, or blood oxygen.

Currently, for measurement of the blood pressure, a plurality of measurement methods exist on the market. For example, the following several measurement methods are listed. A first blood pressure measurement method is a cuff inflation method. A second blood pressure measurement method is obtaining a blood pressure value based on a pulse transmission time (PTT). A third blood pressure measurement method is obtaining a blood pressure value based on a waveform of a photoplethysmography (PPG) signal. A fourth blood pressure measurement method is obtaining a blood pressure value based on a fingertip pressure and a waveform of a PPG signal of a fingertip.

However, when these existing methods are used on the wearable device for blood pressure measurement, a problem that the blood pressure value obtained through measurement is inaccurate exists.

SUMMARY

This application provides a blood pressure measurement method for a wearable device and a wearable device, so as to improve measurement accuracy of a blood pressure value.

According to a first aspect, a blood pressure measurement method for a wearable device is provided. The wearable device includes a pressure transducer (PT) and a photoplethysmography (PPG) module. The PT and the PPG module are deployed at a target position of the wearable device. The target position includes a position for contacting a wearer when the wearable device is in a worn state. The method includes: obtaining a pressure value collected by the PT; obtaining a PPG signal collected by the PPG module; and determining a blood pressure value of the wearer based on the pressure value and the PPG signal.

The target position may refer to a position where the PPG module is deployed. In this application, the PT is added. The PT may also be deployed at each target position. A positional relationship between the PT and the PPG module is not limited in this application.

A position for contacting the wearer when the wearable device is in the worn state may be a bottom of the wearable device. When the wearable device is in the worn state, the bottom of the wearable device may contact skin of the wearer (for example, skin at a wrist and skin at an arm). The wearer may also be referred to as a user. This is not limited in this application.

The PPG module is configured to collect the PPG signal. Therefore, the PPG module may include a light emitting device (for example, a light emitting diode) and a light receiving device (for example, a photo diode). A structure of the PPG module and a positional relationship between the PPG module and the PT are not limited in this application.

The PT may be configured to collect a pressure value between a contact part (a contact part between the wearable device and the wearer) and the wearable device, and collect a PPG signal of the contact part through the PPG module. The PPG signals are different under different pressure values. In this application, a pressure factor may be considered based on the PPG signal to determine the blood pressure value of the wearer. This helps improve accuracy of the blood pressure value. The contact part may also be referred to as a tested part. This is not limited in this application.

According to the blood pressure measurement method for a wearable device provided in this application, the blood pressure value of the wearer is determined based on the pressure value and the PPG signal, and the blood pressure value of the wearer is determined by considering the pressure factor based on the PPG signal. This helps improve accuracy of the blood pressure value.

With reference to the first aspect, in some implementations of the first aspect, the pressure value includes a plurality of pressure values, the PPG signal includes a plurality of PPG signals, the plurality of pressure values are in one-to-one correspondence with the plurality of PPG signals, and a collection moment of each of the plurality of pressure values is same as that of a corresponding one of the PPG signals. The determining a blood pressure value of the wearer based on the pressure value and the PPG signal includes: respectively extracting waveform features of the plurality of PPG signals; and determining, if a first PPG signal whose waveform feature is less than or equal to a preset waveform feature exists in the plurality of PPG signals, a pressure value corresponding to the first PPG signal as a systolic blood pressure (SBP) in the blood pressure value of the wearer.

When different pressure values exist between the wearable device and the contact part, the wearable device may collect a plurality of pressure values through the PT. The plurality of pressure values may be generated by the wearer by pressing, but this application is not limited thereto.

The wearable device may collect the PPG signal through the PPG module to obtain the plurality of PPG signals when collecting each of the plurality of pressure values. In other words, the plurality of pressure values are in one-to-one correspondence with the plurality of PPG signals, and the collection moment of each of the plurality of pressure values is same as that of the corresponding PPG signal.

The wearable device may respectively extract the waveform features of the plurality of PPG signals through a feature extraction model, and may compare the waveform features of the plurality of PPG signals with the preset waveform feature. If the waveform feature of the first PPG signal is less than or equal to the preset waveform feature, the pressure value corresponding to the first PPG signal is determined as the SBP. The preset waveform feature is used to represent that no apparent waveform feature exists. In other words, a researcher may determine the preset waveform feature based on the waveform features of a large quantity of PPG signals that do not have apparent waveform features. If the waveform feature of the first PPG signal is less than or equal to the preset waveform feature, it indicates that the first PPG signal does not have an apparent waveform feature.

If the first PPG signal has no distinct waveform features, it may indicate that the pressure value is relatively large in this case. A pressure between the wearable device and the contact part may cause blood vessels in the contact part to squeeze and form occlusion, and the systolic blood pressure may be accurately measured in this case.

According to the blood pressure measurement method for a wearable device provided in this application, the pressure value corresponding to the first PPG signal less than or equal to the preset waveform feature is determined as the SBP, and the systolic blood pressure may be directly obtained through the PT. This is simple, efficient, and highly accurate.

With reference to the first aspect, in some implementations of the first aspect, the pressure value includes a plurality of pressure values, the PPG signal includes a plurality of PPG signals, the plurality of pressure values are in one-to-one correspondence with the plurality of PPG signals, and the collection moment of each of the plurality of pressure values is the same as that of the corresponding PPG signal. The determining a blood pressure value of the wearer based on the pressure value and the PPG signal includes: respectively extracting waveform features of the plurality of PPG signals; and inputting the plurality of pressure values and the waveform features of the plurality of PPG signals into a first neural network model, where the first neural network model is trained based on a historical pressure value and a waveform feature of a historical PPG signal, and is configured to measure blood pressure; and determining output of the first neural network model as a diastolic blood pressure (DBP) in the blood pressure value of the wearer.

The researcher may train the first neural network model based on the historical pressure value and the waveform feature of the historical PPG signal to determine the DBP in the blood pressure value.

The wearable device may use the plurality of pressure values and the waveform features of the plurality of PPG signals as the input to the first neural network model, and determine the output of the first neural network model as the DBP.

Optionally, the wearable device may use a pressure value of the plurality of pressure values that is less than or equal to the pressure value corresponding to the first PPG signal (that is, the PPG signal that does not have an apparent waveform feature) and the PPG signal corresponding to the pressure value as the input to the first neural network model, and determine the output of the first neural network model as the DBP.

According to the blood pressure measurement method for a wearable device provided in this application, the diastolic blood pressure is calculated through the waveform feature presented by the pressure value and the PPG signal. Compared with the blood pressure value calculated through regression or another calculation method, accuracy of the blood pressure value is improved.

With reference to the first aspect, in some implementations of the first aspect, before the obtaining a pressure value collected by the PT, the foregoing method further includes: outputting an operation guide, where the operation guide is configured to guide the wearer to apply a pressure perpendicular to a contact surface between the wearable device and human skin to the wearable device, and the operation guide includes a pressure value required for the wearer to press.

The pressure value between the wearable device and the contact part may be generated by the wearer by pressing based on the operation guide. The wearable device may guide the user to continuously apply a pressure to the wearable device through texts, sound, an image, or a color. In other words, the operation guide may be the texts, the sound, the image, or the color. This is not limited in this application. In a possible implementation, the operation guide may be "please increase the pressing pressure". The wearable device may guide the user through the sound and/or the texts. In another possible implementation, the wearable device displays a pressure curve through a human-machine interaction interface, and guides the user to continuously apply the pressure to the wearable device based on the pressure curve.

The wearable device may guide the user to continuously apply the pressure to the wearable device over a period of time based on the operation guide. The continuously applied pressure is perpendicular to the contact surface between the wearable device and the human skin (the contact part or the tested part), so that a continuous pressure change is generated between the wearable device and the human skin. A duration for the continuous pressure application is not limited in embodiments of this application. In a possible implementation, the duration for the continuous pressure application may be 30 seconds.

It is to be noted that the process of continuous pressure application is a process of increasing the pressure. In this embodiment of this application, the blood vessels in the skin in contact with the wearable device are squeezed to form the occlusion through the continuous pressure application by the user, so as to measure the blood pressure.

According to the blood pressure measurement method for a wearable device provided in this application, the wearer is guided to apply the pressure through the operation guide, so as to regulate a pressure application behavior of the wearer. The applied pressure is controllable and is an expected pressure value. This is helpful for measurement of a subsequent blood pressure value.

With reference to the first aspect, in some implementations of the first aspect, the foregoing method further includes: ending, during the pressure application by the wearer, blood pressure measurement if the following condition is satisfied: an acceleration of the wearable device is greater than an acceleration threshold; and/or an angular velocity of the wearable device is greater than an angular velocity threshold.

During the pressure application by the wearer, that is, during the pressure application by the wearer based on the operation guide, the wearable device may detect a stability situation during the pressure application. If the stability situation does not satisfy a data collection requirement, the blood pressure measurement is ended.

If the acceleration of the wearable device is greater than the acceleration threshold, it may indicate that the wearable device is in a shaking state and the requirement is not satisfied, and the blood pressure measurement is ended. If the angular velocity of the wearable device of the wearable device is greater than the angular velocity threshold, it may indicate that the wearable device is in a skewed or warped state and the requirement is not satisfied, and the blood pressure measurement is ended. If the acceleration of the wearable device is greater than the acceleration threshold, and the angular velocity of the wearable device of the wearable device is greater than the angular velocity threshold, it may indicate that the wearable device is in the shaking state and the skewed or warped state and the requirement is not satisfied, and the blood pressure measurement is ended. The acceleration of the wearable device may be obtained through an accelerometer, and the angular velocity of the wearable device may be obtained through a gyroscope, but this application is not limited thereto.

According to the blood pressure measurement method for a wearable device provided in this application, the state of the wearable device is detected during pressure application by the wearer. When the wearable device is in an unstable state, the blood pressure measurement is ended. This helps cause the blood pressure measurement to be performed in a stable situation and ensure accuracy of the blood pressure measurement.

With reference to the first aspect, in some implementations of the first aspect, the foregoing method further includes: displaying a first interface, where a pressing position, prompt information, a pressure curve, and a waveform of the PPG signal are displayed on the first interface, the pressing position is a position where the wearer applies the pressure to the wearable device, the prompt information is used to prompt the wearer to apply the pressure to the wearable device based on the operation guide, and the pressure curve is the operation guide.

The first interface may also be referred to as an interface. This is not limited in embodiments of this application. The pressing position is a position where the wearer applies the pressure to the wearable device, which may be one position or a plurality of positions. This is not limited in embodiments of this application. The pressing position is also a specified position in this embodiment. To be specific, the pressing position may be a center, an upper side and a lower side, or a left side and a right side of a screen of the wearable device. This is not limited in embodiments of this application. The pressure curve is the operation guide. The wearer may apply the pressure to the wearable device based on the pressure curve, and the wearable device may guide the user to correctly apply the pressure through the prompt information. The waveform of the PPG signal may be the waveform of the PPG signal collected by the wearable device. In a possible implementation, the first interface may be an interface shown in FIG. 13 in the embodiment.

According to the blood pressure measurement method for a wearable device provided in this application, the pressing position, the prompt information, the pressure curve, and the waveform of the PPG signal are displayed through the first interface. This is helpful for the user to correctly apply the pressure to the wearable device based on the operation guide, may improve user experience, and is also helpful to ensure correct measurement of the blood pressure value.

With reference to the first aspect, in some implementations of the first aspect, the pressing position includes a first position and a second position of a screen of the wearable device, the first position is pressed by an index finger of the wearer, and the second position is pressed by a thumb of the wearer.

The wearable device may guide the wearer to apply the pressure to the wearable device at the first position of the screen by using the index finger and at the second position of the screen by using the thumb. Compared with a situation of pressing one position, it is more conducive to ensuring stability of the wearable device during the pressure application.

With reference to the first aspect, in some implementations of the first aspect, the foregoing method further includes: displaying the blood pressure value on the first interface.

After the wearable device calculates the blood pressure value, the wearable device may also display the blood pressure value on the foregoing first interface. This helps cause the wearer to determine that the blood pressure value has been obtained and pressure may be no longer applied to the wearable device.

With reference to the first aspect, in some implementations of the first aspect, before the obtaining a pressure value collected by the PT, the foregoing method further includes: detecting a triggering operation performed by the wearer on an automatic blood pressure measurement option; and determining, in response to the triggering operation performed by the wearer on the automatic blood pressure measurement option, whether a measurement time is reached; and the obtaining a pressure value collected by the PT includes: obtaining the pressure value collected by the PT when the measurement time is reached.

This application may provide an automatic blood pressure measurement option for the wearer. When the triggering operation performed by the wearer on the automatic blood pressure measurement option is detected, in response to the triggering operation performed by the wearer on the automatic blood pressure measurement option, the blood pressure value of the wearer may be measured at a preset measurement time or a measurement time set by the wearer.

According to the blood pressure measurement method for a wearable device provided in this application, the blood pressure may be automatically measured when the measurement time is reached without perception of the user. This may satisfy different measurement scenes and is more conducive to user experience.

With reference to the first aspect, in some implementations of the first aspect, the determining a blood pressure value of the wearer based on the pressure value and the PPG signal includes: inputting, if historical data includes the pressure value, the pressure value, a waveform feature of a PPG signal corresponding to the pressure value in the historical data, and a waveform feature of the PPG signal into a second neural network model, to obtain the blood pressure value, where the historical data is used to represent measured data during historical blood pressure measurement, and the second neural network model is trained based on a historical pressure value and a historical PPG signal and is configured for the blood pressure measurement.

The second neural network model may be the same as the first neural network model described above, or may be different from the first neural network model. This is not limited in embodiments of this application. If the second neural network model is the same as the first neural network model, the first neural network model may also output the SBP and the DBP in the blood pressure value. However, only the DBP is used in the foregoing solution.

The historical data may be measured data during the historical measurement of the blood pressure. In other words, the wearable device saves, as the historical data for subsequent automatic measurement, the blood pressure value obtained when the wearer measures the blood pressure.

If the historical data includes the blood pressure value collected by the PT, the wearable device may also input the waveform feature of the PPG signal corresponding to the pressure value in the historical data into the second neural network model based on the waveform feature of the PPG signal, to increase the feature of the PPG signal.

This helps improve measurement accuracy of the blood pressure value.

With reference to the first aspect, in some implementations of the first aspect, the determining a blood pressure value of the wearer based on the pressure value and the PPG signal includes: inputting, if historical data does not include the pressure value, the pressure value and a waveform feature of the PPG signal into the second neural network model to obtain a temporary blood pressure value, where the historical data is used to represent measured data during historical blood pressure measurement; and determining the blood pressure value based on the temporary blood pressure value and a blood pressure value in the historical data.

If the historical data does not include the blood pressure value collected by the PT, the wearable device may input the pressure value and the waveform feature of the PPG signal into the second neural network model to obtain the temporary blood pressure value. To ensure accuracy of the measured blood pressure value, the blood pressure value in the historical data is obtained, and a current measured blood pressure value is determined based on the temporary blood pressure value and the blood pressure value in the historical data. For example, the blood pressure value in the historical data may have different weight coefficients. A sum of the weight coefficient of the current blood pressure value and a weight coefficient of a historical blood pressure value is 1. The blood pressure value may be a sum of the historical blood pressure value and a corresponding weight coefficient thereof plus a sum of the temporary blood pressure value and a corresponding weight coefficient thereof.

With reference to the first aspect, in some implementations of the first aspect, before the obtaining a pressure value collected by the PT, the foregoing method further includes: determining whether the wearable device satisfies a measurement condition; and the obtaining a pressure value collected by the PT includes: obtaining the pressure value collected by the PT when the measurement condition is satisfied.

The wearable device determines whether the measurement condition is satisfied. In other words, the wearable device determines whether the blood pressure measurement may be performed in this case. If the measurement condition is satisfied, it may indicate that the blood pressure measurement may be effectively performed in a current state, and the blood pressure value has relatively high accuracy. If the measurement condition is not satisfied, it may indicate that the blood pressure measurement cannot be effectively performed in the current state, and the blood pressure value has relatively low accuracy.

The measurement condition may include at least one of the wearable device being in a relatively static state, the wearable device being in good contact with the skin, and the PPG signal having good quality.

The wearable device may obtain the acceleration of the wearable device through an accelerometer (ACC) to determine whether the wearable device is in the relatively static state. The wearable device may obtain the pressure value through the PT to determine whether the wearable device is in good contact with the skin. The wearable device may determine, through the waveform feature of the PPG signal, whether the PPG signal has good quality. However, this embodiment of this application is not limited thereto.

According to the blood pressure measurement method for a wearable device provided in this application, it is determined whether the measurement condition is satisfied before the blood pressure measurement is performed. Measurement is performed based on the measurement condition that is satisfied, which helps improve accuracy of the blood pressure value.

With reference to the first aspect, in some implementations of the first aspect, the foregoing measurement condition includes at least one of the following: the acceleration of the wearable device is less than or equal to the acceleration threshold, an initial pressure value is greater than or equal to a pressure threshold, the angular velocity of the wearable device is less than or equal to the angular velocity threshold, or an initial PPG signal satisfies a signal quality requirement, where the acceleration is used to represent a contact situation between the wearable device and the wearer, and the initial pressure value is used to represent a tightness for wearing the wearable device.

With reference to the first aspect, in some implementations of the first aspect, the foregoing method further includes: prompting the wearer to wear the wearable device properly when the measurement condition is not satisfied.

According to the blood pressure measurement method for a wearable device provided in this application, when the measurement condition is not satisfied, the wearer is prompted to wear the wearable device properly. This helps cause the wearer to correctly wear the wearable device, thereby improving the measurement accuracy of the blood pressure value.

With reference to the first aspect, in some implementations of the first aspect, the foregoing PPG module includes 3 light emitting diodes LEDs and 3 photo diodes PDs, the PT is located at a central position of the PPG module, and the 3 LEDs and the 3 PDs are respectively spaced apart from each other around the PT.

Through this implementation, the LEDs and the PDs are spaced apart from each other. This helps the PG receive an optical signal. The PT is located at the central position of the PPG module. This helps save memory space.

With reference to the first aspect, in some implementations of the first aspect, the foregoing PPG module includes 3 LEDs and 1 PD, the PT includes 3 PTs, the PD is located at the central position of the PPG module, and the 3 LEDs and the 3 PTs are all arranged around the PD in a circular array.

Through this implementation, when a housing of the wearable device contacts human skin, 3 pressure transducers may respectively measure pressure values. Based on a distribution of the pressure values, it may be determined whether the pressure is uniformly applied to the wearable device, thereby improving the measurement accuracy.

With reference to the first aspect, in some implementations of the first aspect, the foregoing PPG module includes 4 LEDs and 4 PDs, the PT is located at a central position of the PPG module, and the 4 LEDs and the 4 PDs are respectively spaced apart from each other around the PT.

Through this implementation, a relatively large quantity of LEDs and PDs are provided. The relatively large quantity of PDs may collect more optical signals on the same optical path, and the collected optical signals are strong, which results in strong electrical signals generated therefrom and thus strong PPG signals, so as to improve quality of the PPG signal.

According to a second aspect, a wearable device is provided. The wearable device includes a pressure transducer (PT) and a photoplethysmography (PPG) module. The PT and the PPG module are deployed at a target position of the wearable device. The target position includes a position for contacting a wearer when the wearable device is in a worn state. The wearable device includes: an obtaining module and a processing module, where the obtaining module is configured to obtain a pressure value collected by the PT; obtain a PPG signal collected by the PPG module; and the processing module is configured to determine a blood pressure value of the wearer based on the pressure value and the PPG signal.

With reference to the second aspect, in some implementations of the second aspect, the pressure value includes a plurality of pressure values, the PPG signal includes a plurality of PPG signals, the plurality of pressure values are in one-to-one correspondence with the plurality of PPG signals, and a collection moment of each of the plurality of pressure values is same as that of a corresponding one of the PPG signals. The foregoing processing module is further configured to: respectively extract waveform features of the plurality of PPG signals; and determine, if a first PPG signal whose waveform feature is less than or equal to a preset waveform feature exists in the plurality of PPG signals, a pressure value corresponding to the first PPG signal as a systolic blood pressure SBP in the blood pressure value of the wearer.

With reference to the second aspect, in some implementations of the second aspect, the pressure value includes a plurality of pressure values, the PPG signal includes a plurality of PPG signals, the plurality of pressure values are in one-to-one correspondence with the plurality of PPG signals, and the collection moment of each of the plurality of pressure values is the same as that of the corresponding PPG signal. The foregoing processing module is further configured to: respectively extract waveform features of the plurality of PPG signals; input the plurality of pressure values and the waveform features of the plurality of PPG signals into a first neural network model, where the first neural network model is trained based on a historical pressure value and a waveform feature of a historical PPG signal, and is configured to measure blood pressure; and determine an output of the first neural network model as a diastolic blood pressure DBP in the blood pressure value of the wearer.

With reference to the second aspect, in some implementations of the second aspect, the foregoing processing module is further configured to output an operation guide, where the operation guide is configured to guide the wearer to apply a pressure perpendicular to a contact surface between the wearable device and human skin to the wearable device, and the operation guide includes a pressure value required for the wearer to press.

With reference to the second aspect, in some implementations of the second aspect, the foregoing processing module is further configured to end, during the pressure application by the wearer, blood pressure measurement if the following condition is satisfied: an acceleration of the wearable device is greater than an acceleration threshold; and/or an angular velocity of the wearable device is greater than an angular velocity threshold.

With reference to the second aspect, in some implementations of the second aspect, the foregoing wearable device further includes a display module. The display module is configured to display a first interface, where a pressing position, prompt information, a pressure curve, and a waveform of the PPG signal are displayed on the first interface, the pressing position is a position where the wearer applies the pressure to the wearable device, the prompt information is used to prompt the wearer to apply the pressure to the wearable device based on the operation guide, and the pressure curve is the operation guide.

With reference to the second aspect, in some implementations of the second aspect, the foregoing pressing position includes a first position and a second position of a screen of the wearable device, the first position is pressed by an index finger of the wearer, and the second position is pressed by a thumb of the wearer.

With reference to the second aspect, in some implementations of the second aspect, the foregoing wearable device further includes a display module. The display module is configured to display the blood pressure value on the first interface.

With reference to the second aspect, in some implementations of the second aspect, the foregoing processing module is further configured to detect a triggering operation performed by the wearer on an automatic blood pressure measurement option; and determine, in response to the triggering operation performed by the wearer on the automatic blood pressure measurement option, whether a measurement time is reached. The foregoing obtaining module is further configured to obtain the pressure value collected by the PT when the measurement time is reached.

With reference to the second aspect, in some implementations of the second aspect, the foregoing processing module is further configured to input, if historical data includes the pressure value, the pressure value, a waveform feature of a PPG signal corresponding to the pressure value in the historical data, and a waveform feature of the PPG signal into a second neural network model, to obtain the blood pressure value, where the historical data is used to represent measured data during historical blood pressure measurement, and the second neural network model is trained based on a historical pressure value and a historical PPG signal and is configured for the blood pressure measurement.

With reference to the second aspect, in some implementations of the second aspect, the foregoing processing module is further configured to input, if historical data does not include the pressure value, the pressure value and a waveform feature of the PPG signal into the second neural network model to obtain a temporary blood pressure value, where the historical data is used to represent measured data during historical blood pressure measurement; and determining the blood pressure value based on the temporary blood pressure value and a blood pressure value in the historical data.

With reference to the second aspect, in some implementations of the second aspect, the foregoing processing module is further configured to determine whether the wearable device satisfies a measurement condition. The foregoing obtaining module is further configured to obtain the pressure value collected by the PT when the measurement condition is satisfied.

With reference to the second aspect, in some implementations of the second aspect, the foregoing measurement condition includes at least one of the following: the acceleration of the wearable device is less than or equal to the acceleration threshold, an initial pressure value is greater than or equal to a pressure threshold, the angular velocity of the wearable device is less than or equal to the angular velocity threshold, or an initial PPG signal satisfies a signal quality requirement, where the acceleration is used to represent a contact situation between the wearable device and the wearer, and the initial pressure value is used to represent a tightness for wearing the wearable device.

With reference to the second aspect, in some implementations of the second aspect, the foregoing processing module is further configured to prompting the wearer to wear the wearable device properly when the measurement condition is not satisfied.

With reference to the second aspect, in some implementations of the second aspect, the foregoing PPG module includes 3 light emitting diodes LEDs and 3 photo diodes PDs, the PT is located at a central position of the PPG module, and the 3 LEDs and the 3 PDs are respectively spaced apart from each other around the PT.

With reference to the second aspect, in some implementations of the second aspect, the foregoing PPG module includes 3 LEDs and 1 PD, the PT includes 3 PTs, the PD is located at the central position of the PPG module, and the 3 LEDs and the 3 PTs are all arranged around the PD in a circular array.

With reference to the second aspect, in some implementations of the second aspect, the foregoing PPG module includes 4 LEDs and 4 PDs, the PT is located at a central position of the PPG module, and the 4 LEDs and the 4 PDs are respectively spaced apart from each other around the PT.

According to a third aspect, this application provides a wearable device, which may also be referred to as a blood pressure measurement apparatus, including a processor. The processor is coupled to a memory, and may be configured to execute an instruction in the memory, to implement the method according to any one of the possible implementations of the foregoing first aspect. Optionally, the wearable device further includes a memory. Optionally, the wearable device further includes a transceiver. The processor is coupled to the transceiver.

According to a fourth aspect, this application provides a processor, including an input circuit, an output circuit, and a processing circuit. The processing circuit is configured to receive a signal by using the input circuit and transmit a signal by using the output circuit, so that the processor performs the method according to any one of the possible implementations of the foregoing first aspect.

In a specific implementation process, the foregoing processor may be a chip, the input circuit may be an input pin, the output circuit may be an output pin, and the processing circuit may be a transistor, a gate circuit, a flip-flop, various logic circuits, and the like. An inputted signal received by the input circuit may be for example without limitation received and inputted by a receiver, a signal outputted by the output circuit may be for example without limitation outputted to and transmitted by a transmitter, and the input circuit and the output circuit may be a same circuit. The circuit is used as the input circuit and the output circuit at different moments. Specific implementations of the processor and various circuits are not limited in this application.

According to a fifth aspect, this application provides a processing apparatus, including a processor and a memory. The processor is configured to read an instruction stored in the memory, and may receive a signal by using a receiver and transmit a signal by using a transmitter, to perform the method according to any one of the possible implementations of the foregoing first aspect.

Optionally, one or more processors are provided, and one or more memories are provided.

Optionally, the memory may be integrated with the processor, or the memory is arranged separately from the processor.

In a specific implementation process, the memory may be a non-transitory memory, for example, a read-only memory (ROM). The memory and the processor may be integrated on a same chip, or may be separately arranged on different chips. A type of the memory and a manner of arranging the memory and the processor are not limited in this application.

It is to be understood that a related data interaction process, for example, sending indication information, may be a process of outputting indication information from the processor, and receiving capability information may be a process of receiving input capability information by the processor. Specifically, data outputted by the processing may be outputted to the transmitter, and input data received by the processor may be from the receiver. The transmitter and the receiver may be collectively referred to as a transceiver.

The processing apparatus in the foregoing fifth aspect may be a chip. The processor may be implemented by hardware, or may be implemented by software. When the processor is implemented by hardware, the processor may be a logic circuit, an integrated circuit, and the like. When the processor is implemented through software, the processor may be a general-purpose processor, and is implemented by reading software code stored in a memory. The memory may be integrated into the processor, may be located outside the processor, or may exist independently.

According to a sixth aspect, this application provides a computer-readable storage medium. The computer-readable storage medium stores a computer program (which may also be referred to as code or an instruction). When the computer program is run on a computer, the computer is enabled to perform the method in any one of the possible implementations of the foregoing first aspect.

According to a seventh aspect, this application provides a computer program product. The computer program product includes a computer program (which may also be referred to as code or an instruction). When the computer program is run, the computer is enabled to perform the method according to any one of the possible implementations of the foregoing first aspect.

BRIEF DESCRIPTION OF DRAWINGS

FIG. 10 is a schematic flowchart of a method for calculating a blood pressure value according to an embodiment of this application;

FIG. 14A and FIG. 14B are schematic flowcharts of still another blood pressure measurement method for a wearable device according to an embodiment of this application;

DESCRIPTION OF EMBODIMENTS

Figure 1:
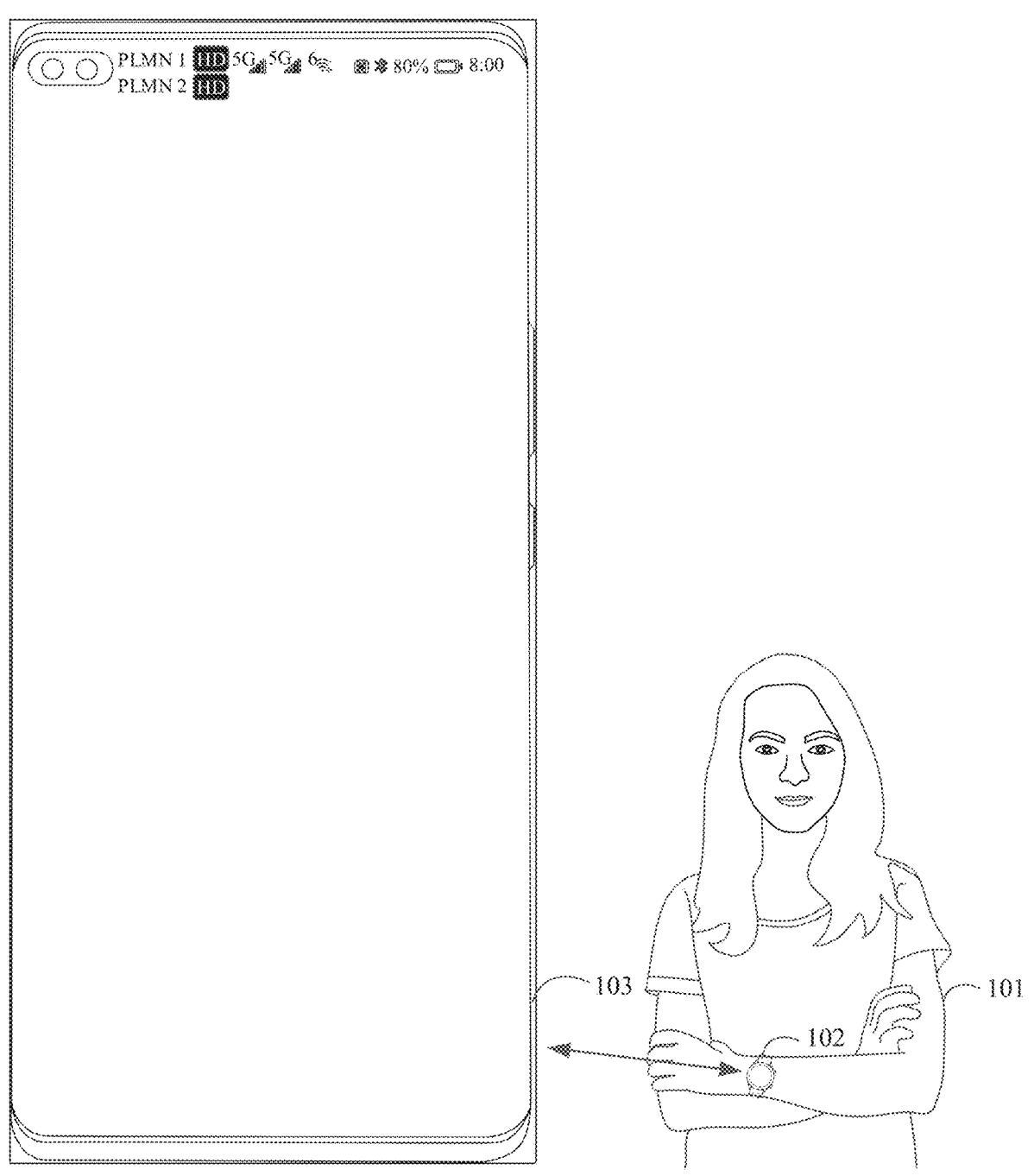
FIG. 1 is a schematic diagram of a blood pressure measurement scene according to an embodiment of this application.

The following describes technical solutions of this application with reference to the accompanying drawings.

Currently, a plurality of blood pressure measurement methods exist on the market, and through research on various measurement methods in this application, it is found that accuracy of a blood pressure value is difficult to guarantee.

A common blood pressure measurement manner is that a smartwatch measures blood pressure by using a cuff inflation method. The cuff inflation method is using a pressure formed after a cuff airbag is inflated to cause blood vessels of a tested part to be squeezed, and using a pressure transducer (PT) to measure a direct pressure value in the airbag to measure the blood pressure.

Through research on the principle of the method in this application, and it is found that the cuff inflation method can only directly measure a maximum mean arterial pressure of the tested part of a human body. An arterial pressure curve is not directly related to the blood pressure value in theory. A manufacturer obtains a coefficient relationship between the blood pressure value and the measured maximum mean arterial pressure through a large quantity of data statistics, and then calculates the blood pressure value. A theoretical basis of conversion between the maximum mean arterial pressure and the blood pressure value is weak, resulting in an inaccurate blood pressure value. In addition, the airbag has a limited service life, needs to be regularly disassembled and replaced, and occupies a large space. The operation is cumbersome, and maintenance is difficult. In addition, the airbag causes the smartwatch to be thick and heavy, and affects wearing experience of a user.

Another common blood pressure measurement manner is obtaining a blood pressure value based on pulse transmission time (PTT). The method is a method for indirectly measuring blood pressure. A blood pressure measurement device may obtain the pulse transmission time based on an electrocardiogram (ECG) and photoplethysmography (PPG), and calculate a blood pressure value through the pulse transmission time.

Through research on the principle of the method in this application, and it is found that a transmission time of a pulse wave is related to time when cardiac ejection begins. The time when the cardiac ejection begins cannot be accurately measured, causing an inaccurate transmission time of the pulse wave, and further leading to an inaccurate blood pressure value. In addition, different people have different blood vessels, and a model used in the method cannot be applied to all people.

Still another common blood pressure measurement manner is obtaining a blood pressure value based on a waveform of a PPG signal. The waveform of the PPG signal may also be referred to as a pulse wave waveform, and includes important feature information of human blood pressure. In general, a main peak of the waveform of the PPG signal corresponds to a systolic blood pressure, and a replay wave peak corresponds to a diastolic blood pressure. The blood pressure measurement device includes a PPG module. The PPG module contacts human skin to collect a PPG signal of a human body.

Through research on the method in this application, it is found that the method has a high requirement for a wearing tightness. If the human skin is in poor contact with the PPG module, the PPG signal is inaccurate, and then the blood pressure value is inaccurate.

Another common blood pressure measurement manner is obtaining a blood pressure value based on a fingertip pressure and a waveform of a PPG signal of a fingertip. A user applies a pressure to a wearable device through the fingertip, so that the wearable device is in good contact with a contact part of the user, collects a PPG signal of the fingertip, and obtains the blood pressure value based on the waveform of the PPG signal of the fingertip.

Through research on the principle of the method in this application, it is found that a muscle of the fingertip contracts when the pressure is applied to the fingertip. In this case, a great difference exists between the waveform of the PPG signal and the waveform of the PPG signal when the fingertip is in a relaxed state. However, the blood pressure value is relatively accurate when a tested part (that is, the fingertip) is in the relaxed state. Therefore, the blood pressure value measured according to the method is inaccurate. In addition, if the user uses fingertips of different fingers to press, a difference in different fingertips leads to different quality of generated PPG signals and different blood pressure values. As a result, a correct blood pressure value cannot be obtained.

In addition, through the plurality of blood pressure measurement manners described above, blood pressure measurement can only be performed when the user has a requirement for the blood pressure measurement, and the blood pressure cannot be actively measured. In other words, the blood pressure cannot be measured autonomously or periodically. This is not helpful to monitor human body data and cannot satisfy a requirement of the user for health management.

In view of this, embodiments of this application provide a blood pressure measurement method for a wearable device and a wearable device. The user is guided to apply the pressure perpendicular to the wearable device to the wearable device, so that a pressure is formed between the wearable device and the human skin (that is, the tested part, that is, a part that contacts the wearable device). The pressure value between the wearable device and the human skin during the pressure application is obtained through the PT, the PPG signal of the human skin under the pressure value is collected through the PPG module, and the blood pressure value is calculated based on the pressure value and the waveform feature of the PPG signal. Specifically, according to the method, the systolic blood pressure (that is, a high pressure) of the blood pressure may be directly measured through the PT, and the diastolic blood pressure (that is, a low pressure) is calculated through the waveform feature presented by the PPG signal. Compared with the blood pressure value calculated through regression or another calculation method, accuracy of the blood pressure value is improved. In addition, according to the method, the pressure value between the wearable device and skin is collected. In this case, the tested part is in a relaxed state, so as to avoid interference and influence of the foregoing fingertip pressing on the PPG signal. According to the method, it may also be determined whether the wearable device satisfies the measurement condition before the blood pressure measurement, so as to avoid a problem of an inaccurate blood pressure measurement result as a result of a tightness for wearing the wearable device, a contact condition of the human skin, and a difference in physical properties of skin. According to the blood pressure measurement method for a wearable device provided in this embodiment of this application, blood pressure may also be measured autonomously or periodically. This is helpful to monitor human body data and satisfy the requirement of the user for health management.

To have a better understanding of embodiments of this application, an embodiment of this application provides a blood pressure measurement scene.

For example, FIG. 1 is a schematic diagram of a blood pressure measurement scene. As shown in FIG. 1, the blood pressure measurement scene includes a user 101, a wearable device 102, and a terminal device 103. The user 101 wears the wearable device 102 on a wrist. The wearable device 102 may support a function of blood pressure measurement. The terminal device 103 may perform data communication with the wearable device 102.

In the scene, this embodiment of this application provides two blood pressure measurement methods for a wearable device.

For a first blood pressure measurement method for a wearable device, the wearable device 102 may include a PT, a PPG module, and an accelerometer (ACC). The wearable device 102 may obtain an acceleration of the wearable device 102 through the ACC, and may determine, based on the acceleration, whether the wearable device 102 is in a relatively static state. When the wearable device 102 is in the relatively static state, a pressure value between a bottom of the wearable device 102 and skin of the wrist is obtained through the PT, a PPG signal of a blood vessel of the wrist is obtained through the PPG module, and a blood pressure value is calculated based on the pressure value and the PPG signal. The wearable device 102 may transmit a measured blood pressure value to the terminal device 103. The terminal device 103 may save and display the blood pressure value.

For a second blood pressure measurement method for a wearable device, the wearable device 102 may include a PT, a PPG module, and an ACC. The wearable device 102 may obtain an acceleration of the wearable device 102 through the ACC, and determine, based on the acceleration, whether the wearable device 102 is in a relatively static state. When the wearable device 102 is in the relatively static state, a pressure value between a bottom of the wearable device 102 and skin of the wrist is obtained through the PT, and a PPG signal of a blood vessel of the wrist is obtained through the PPG module. The wearable device 102 may transmit the pressure value and the PPG signal to the terminal device 103. The terminal device 103 may calculate a blood pressure value based on the pressure value and the PPG signal. The terminal device 103 may save and display the blood pressure value. The terminal device 103 may also transmit the blood pressure value to the wearable device 102. The wearable device 102 may save and display the blood pressure value.

According to the blood pressure measurement method for a wearable device, computing power of the wearable device 102 may be saved, and power consumption of the wearable device 102 may be reduced.

To have a better understanding of embodiments of this application, the following describes a structure of a communication system in embodiments of this application. For example, FIG. 2 is a schematic structural diagram of a communication system according to an embodiment of this application.

Figure 2:
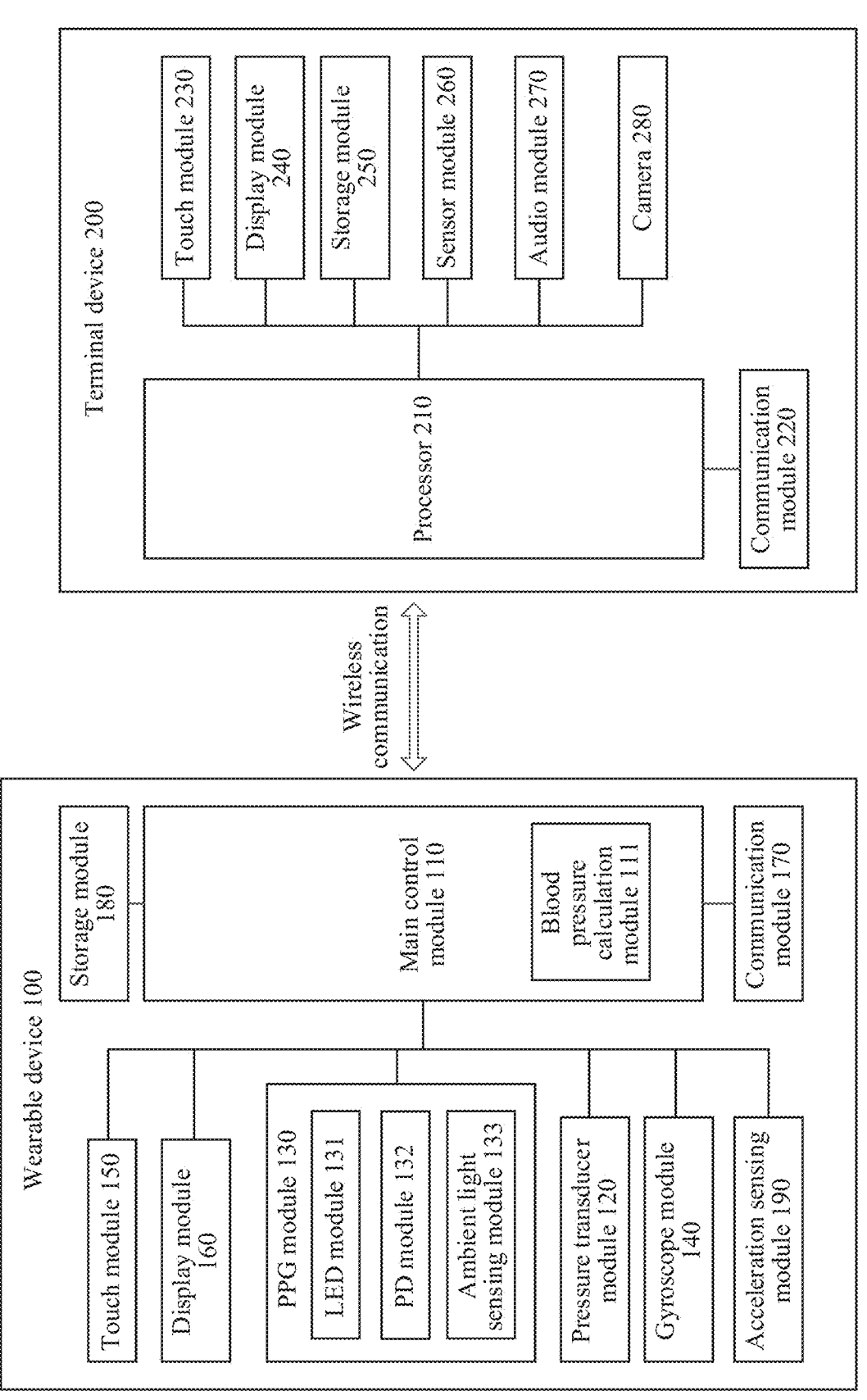
FIG. 2 is a schematic structural diagram of a communication system according to an embodiment of this application.

As shown in FIG. 2, the communication system may include a wearable device 100 and a terminal device 200.

The wearable device 100 may be a smartwatch, a smart bracelet, or the like. This is not limited in embodiments of this application. A specific technology and a specific device form used by the wearable device are not limited in embodiments of this application.

The terminal device 200 may be a device such as a mobile phone or a tablet computer. This is not limited in embodiments of this application. A specific technology and a specific device form used by the terminal device are not limited in embodiments of this application.

As shown in FIG. 2, the wearable device 100 and the terminal device 200 may transmit data information to each other through a communication module.

The wearable device 100 may include a main control module 110, a pressure transducer module 120, a PPG module 130, a gyroscope module 140, a touch module 150, a display module 160, a communication module 170, a storage module 180, and an acceleration sensing module 190. The modules may be connected through a bus or in another manner. This is not limited in embodiments of this application.

It may be understood that a schematic structure of this embodiment of the present disclosure does not constitute a specific limitation on the wearable device 100. In some other embodiments of this application, the wearable device 100 may also include more or fewer components than shown in the figure, or some merged components, or some split components, or different component arrangements. The components shown in the figure may be implemented by hardware, software, or a combination of software and hardware.

The main control module 110 may include a blood pressure calculation module 111. The blood pressure calculation module 111 may be configured to calculate a blood pressure value. The main control module 110 may also include one or more processors for supporting other functions of the wearable device 100.

The pressure transducer module 120 may be configured to collect pressure data of the wearable device. In a possible implementation, the pressure transducer module 120 may be configured to collect a pressure value between a bottom of the wearable device and skin of a wrist.

The PPG module 130 may include a light emitting diode (LED) module 131, a (PD) module 132, and an ambient light sensing module 133. The LED module 131 may include one or more LEDs. This is not limited in embodiments of this application. The LED may be a tri-color LED, and the LED may emit a light source such as red light, green light, and infrared light. The PD module 132 may include one or more PDs. This is not limited in embodiments of this application. The PD may be configured to receive an optical signal and process the optical signal into an electrical signal. For example, in a scene of measuring blood pressure, the PD may receive an optical signal reflected by skin tissue and process the signal into an electrical signal. The ambient light sensing module 133 may be an ambient light sensor, and may be configured to sense luminance of ambient light. For example, in a scene of measuring the blood pressure, the ambient light sensor may detect luminance of the LED.

The gyroscope module 140 may be a gyroscope sensor, and may be configured to obtain angular velocity data of the wearable device 100.

The touch module 150 may be a touch sensor. The touch sensor may also be referred to as a "touch control device".

The display module 160 may be a display screen. The touch sensor may be arranged in the display screen, and the touch sensor and the display screen form a touch screen, which may also be referred to as a "touch control screen". The touch sensor may be configured to detect a touch operation performed on or near the touch sensor. The display screen may be configured to display an image, a video, a control, text information, and the like.

The communication module 170 may include a bluetooth communication module and a WLAN communication module. In some embodiments, the WLAN communication module may be integrated with another communication module (for example, the bluetooth communication module). The WLAN communication module and/or the bluetooth module may transmit a signal to detect and scan a device near the wearable device 100, so that the wearable device 100 may discover a nearby device such as the terminal device 200 by using one or more wireless communication technologies such as bluetooth or WLAN. The wearable device 100 may establish a wireless communication connection with the terminal device 200 by using one or more wireless communication technologies such as WLAN and bluetooth, and perform data transmission and data receiving based on the wireless communication connection. The wearable device 100 may transmit data to the terminal device 200 based on one or more wireless communication technologies of the bluetooth communication module or the WLAN communication module. The wearable device 100 may also obtain, through the wireless communication connection, a data instruction transmitted by the terminal device 200.

The storage module 180 is coupled to the main control module 110, and is configured to store various software programs and/or a plurality of sets of instructions. In a specific implementation, the storage module 180 may include a volatile memory, for example, a random access memory (RAM), or may include a non-volatile memory, for example, a ROM, a flash memory, a hard disk drive (HDD), or a solid state drive (SSD). The storage module 180 may also include a combination of the foregoing types of memories. The storage module 180 may store some program code, so that the main control module 110 invokes the program code stored in the storage module 180, to implement the method of embodiments of this application.

The acceleration sensing module 190 may be an accelerometer, and may be configured to detect magnitudes of accelerations of the wearable device 100 in all directions (generally on three axes).

The terminal device 200 may include a processor 210, a communication module 220, a touch module 230, a display module 240, a storage module 250, a sensor module 260, an audio module 270, and a camera 280. The modules may be connected through a bus or in another manner. This is not limited in embodiments of this application.

It may be understood that the schematic structure of this embodiment of the present disclosure does not constitute a specific limitation on the terminal device 200. In some other embodiments of this application, the terminal device 200 may also include more or fewer components than shown in the figure, or some merged components, or some split components, or different component arrangements. The components shown in the figure may be implemented by hardware, software, or a combination of software and hardware.

The processor 210 may include one or more processing units. Different processing units may be independent devices, or may be integrated into one or more processors. A memory may also be arranged in the processor 210 to store an instruction and data.

The communication module 220 may include a mobile communication module and a wireless communication module. The mobile communication module may provide a solution to the wireless communication technology including the $2^{nd}$ generation (2G) communication technology/$3^{rd}$ generation (3G) communication technology/$4^{th}$ generation (4G) communication technology/5th generation (5G) communication technology applied to the terminal device 200. The mobile communication module may include at least one filter, a switch, a power amplifier, a low noise amplifier (LNA), and the like. The wireless communication module may provide solutions to wireless communication technologies including a wireless local area network (WLAN) (such as a wireless fidelity (Wi-Fi) network), bluetooth (BT), a global navigation satellite system (GNSS), frequency modulation (FM), and the like to be applied to the terminal device 200.

The touch module 230 may be a touch sensor. The touch sensor may also be referred to as a "touch control device".

The display module 240 may be a display screen. The touch sensor may be arranged in the display screen, and the touch sensor and the display screen form a touch screen, which may also be referred to as a "touch control screen". The touch sensor may be configured to detect a touch operation performed on or near the touch sensor. The display screen may be configured to display an image, a video, a control, text information, and the like.

The storage module 250 may include an internal memory or an external memory. The external memory may be configured to connect to an external memory card, for example, a Micro SD card, to expand a storage capacity of a terminal device. The external memory card communicates with the processor 210 through the external memory, to implement a data storage function. For example, files such as music and a video are saved in the external memory card. The internal memory may be configured to store computer-executable program code. The executable program code includes an instruction. The internal memory may include a program storage region and a data storage region.

The sensor module 260 may include sensors such as a pressure transducer, a gyroscope sensor, a barometric pressure transducer, a magnetic sensor, an accelerometer, a distance sensor, an optical proximity sensor, a fingerprint sensor, a temperature sensor, an ambient light sensor, a bone conduction sensor, and the like. The pressure transducer is configured to sense a pressure signal, and may convert the pressure signal into an electrical signal. In some embodiments, the pressure transducer may be arranged in the display screen. The gyroscope sensor may be configured to determine a movement posture of the terminal device. The barometric pressure transducer is configured to measure an air pressure. The magnetic sensor includes a Hall sensor. The accelerometer may detect magnitudes of accelerations of the terminal device 200 in all directions (generally on three axes). The distance sensor is configured to measure a distance. The optical proximity sensor may include, for example, a light emitting diode (LED) and an optical detector, for example, a photo diode. The ambient light sensor is configured to sense luminance of ambient light. The fingerprint sensor is configured to collect a fingerprint. The temperature sensor is configured to detect a temperature. The bone conduction sensor may obtain a vibration signal.

The audio module 270 is configured to convert digital audio information into an analog audio signal output, and is also configured to convert an analog audio input into a digital audio signal.

The camera 280 may be configured to capture a static image or a video. In some embodiments, the terminal device may include 1 or N cameras, where N is a positive integer greater than 1.

It is to be noted that the wearable device 100 shown in FIG. 2 provided in this embodiment of this application may perform the foregoing first blood pressure measurement method. In other words, the wearable device 100 determines an operating state of the wearable device 100 by using the data collected by the acceleration sensing module 190, and determines the blood pressure value based on data collected by the pressure transducer 120 and the PPG module 130 through the blood pressure calculation module 111. The wearable device 100 may store the blood pressure value through the storage module 180, and may display the blood pressure value through the display module 160. The wearable device 100 may also transmit the blood pressure value to the terminal device 200 through the communication module 170.

The terminal device 200 may receive the blood pressure value through the communication module 220, may store the blood pressure value into the storage module 250, and may also display the blood pressure value through the display module 240.

Figure 3:
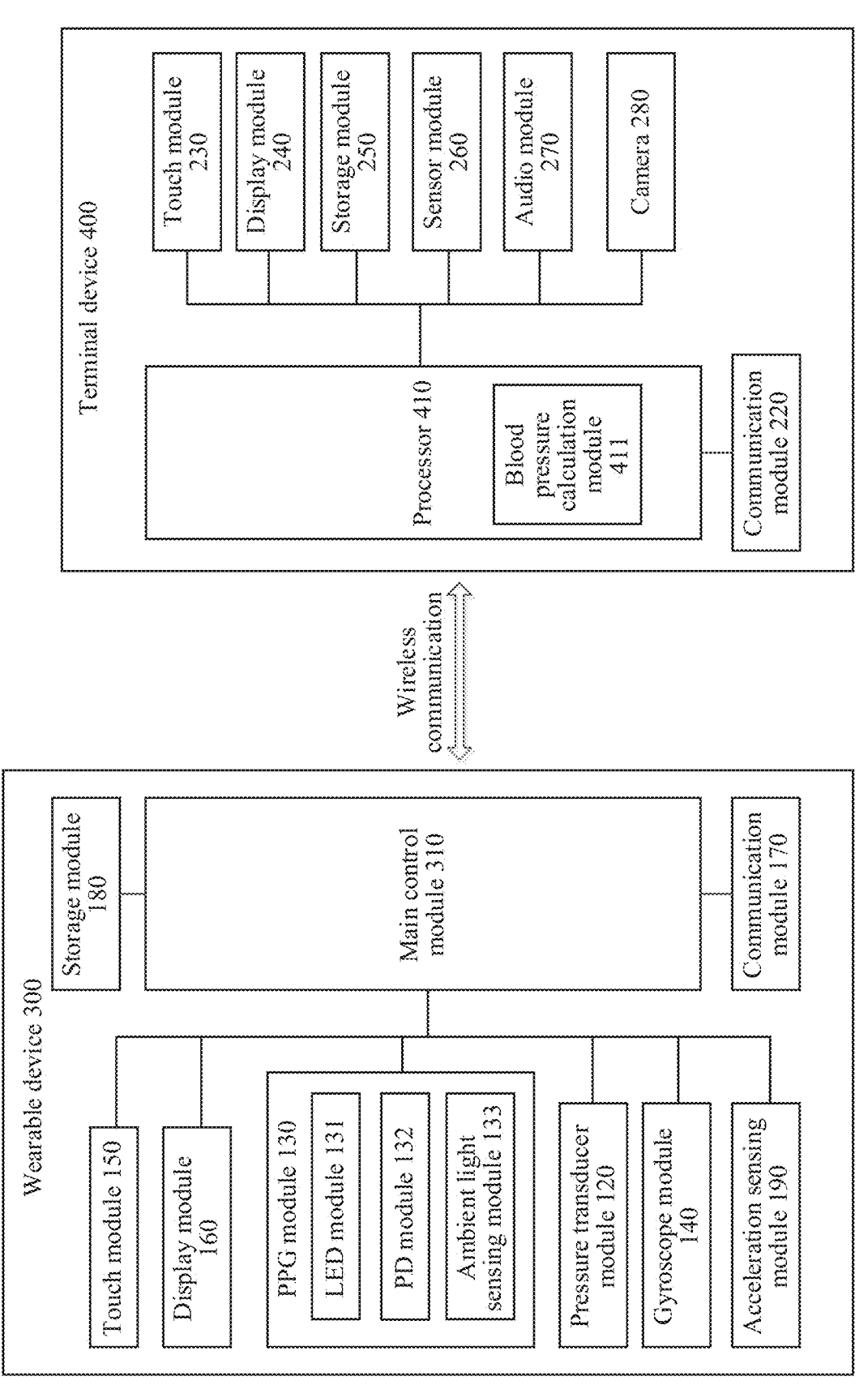
FIG. 3 is a schematic structural diagram of another communication system according to an embodiment of this application.

An embodiment of this application further provides a schematic structural diagram of another communication system. For example, FIG. 3 is a schematic structural diagram of another communication system according to an embodiment of this application. As shown in FIG. 3, the communication system may include a wearable device 300 and a terminal device 400.

The wearable device 300 may be a smartwatch, a smart bracelet, or the like. This is not limited in embodiments of this application. A specific technology and a specific device form used by the wearable device are not limited in embodiments of this application.

The terminal device 400 may be a device such as a mobile phone or a tablet computer. This is not limited in embodiments of this application. A specific technology and a specific device form used by the terminal device are not limited in embodiments of this application.

As shown in FIG. 3, the wearable device 300 and the terminal device 400 may transmit data information to each other through a communication module.

The wearable device 300 may include a main control module 310, a pressure transducer module 120, a PPG module 130, a gyroscope module 140, a touch module 150, a display module 160, a communication module 170, a storage module 180, and an acceleration sensing module 190. The modules may be connected through a bus or in another manner. This is not limited in embodiments of this application.

The main control module 310 may include one or more processors for supporting functions of the wearable device 300. Other modules are all the same as above, and details are not described herein again.

Compared with the foregoing wearable device 100, the wearable device 300 has a different main control module. The main control module 310 in the wearable device 300 is not provided with a blood pressure calculation module 111. In other words, the wearable device 300 cannot calculate the blood pressure value, but may collect data and transmit the data communication module 170 to the terminal device 400. For example, the wearable device 300 collects the data through the pressure transducer 120 and the PPG module 130, and transmits the data to the terminal device 400 through the communication module 170. The wearable device 300 may receive, through the communication module 170, the blood pressure value transmitted by the terminal device 400, store the blood pressure value through the storage module 180, and display the blood pressure value through the display module 160.

The terminal device 400 may include a processor 410, a communication module 220, a touch module 230, a display module 240, a storage module 250, a sensor module 260, an audio module 270, and a camera 280. The modules may be connected through a bus or in another manner. This is not limited in embodiments of this application.

The processor 410 includes a blood pressure calculation module 211. The blood pressure calculation module 211 may be configured to calculate the blood pressure value. The processor 410 may include one or more processing units. Different processing units may be independent devices, or may be integrated into one or more processors. A memory may also be arranged in the processor 410 to store an instruction and data. Other modules are all the same as above, and details are not described herein again.

Compared with the foregoing terminal device 200, the processor 410 of the terminal device 400 includes a blood pressure calculation module 411. In other words, the terminal device 400 may calculate the blood pressure value. Specifically, the terminal device 400 may receive, through the communication module 220, the data transmitted by the wearable device 300, and obtain the blood pressure value based on the data through the blood pressure calculation module 411, may store the blood pressure value into the storage module 250, and may also display the blood pressure value through the display module 240. The terminal device 400 may also transmit the blood pressure value to the wearable device 300 through the communication module 220.

To have a better understanding of embodiments of this application, a schematic diagram of a hardware structure of the wearable device is described in detail in this embodiment of this application.

Figure 4:
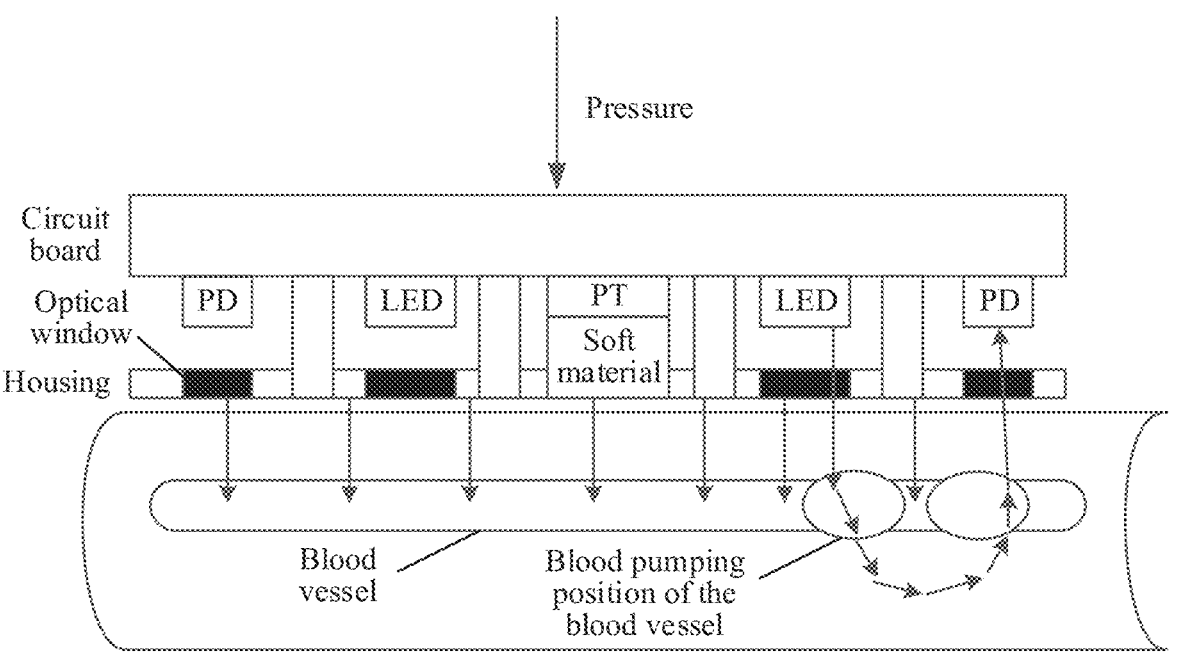
FIG. 4 is a schematic cross-sectional view of a hardware structure of a wearable device according to an embodiment of this application.

For example, FIG. 4 is a schematic cross-sectional view showing a hardware structure of a wearable device. The structure shown in FIG. 4 may be applicable to the wearable device 102, the wearable device 100, and the wearable device 300 described above, but this embodiment of this application is not limited thereto.

As shown in FIG. 4, LEDs, PDs, and a PT are arranged on a circuit board of the wearable device. The PT is deployed at a central position of the circuit board, and the LEDs and the PDs are arranged around the PT. Specific quantities of the LEDs and the PDs are not limited in this application.

Each of the LEDs is a tri-color LED that integrates red light, green light, and infrared light. In other words, an optical signal emitted by the LED may include a green light signal, a red light signal, and an infrared light signal. A wavelength of the optical signal may be in a visible light band or may be in a near-infrared band. This is not limited in embodiments of this application. The LED may also emit an optical signal in another band. This embodiment of this application is not limited thereto.

All of the PDs and the LEDs have optical windows, as shown by black-filled areas in FIG. 4. The green light signal, the red light signal, and the infrared light signal may all pass through the optical windows. Therefore, the optical windows may also be referred to as transparent windows. A material of each of the optical windows may be a commonly used optical transparent material such as polycarbonate (PC), polymethyl methacrylate (PMMA), glass, or sapphire. If the optical signal includes a non-visible light band such as a near-infrared band, the material of the optical window may be a non-transparent optical material that may pass through the near-infrared band.

The optical signal emitted by the LED may be incident on skin through the optical window. The skin includes blood vessels. When blood is pumped into the blood vessels, the blood vessels bulge. Positions where the blood is pumped into the blood vessels are shown by using ellipses in FIG. 4, but this embodiment of this application is not limited thereto. The optical signal is scattered after entering the skin and passing through the blood vessels into which blood is pumped. The scattered signal is in part reflected off the skin, and the optical signal reflected off the skin is received by the PD through the optical window to form an electrical signal. The wearable device may convert the electrical signal into a PPG signal for blood pressure measurement.

The PT is filled with a soft material. The soft material contacts the PT, and a shape thereof matches a housing of the wearable device. When the housing contacts the skin, a pressure formed between the skin and the wearable device is transferred to the PT through the soft material, and the PT may obtain a pressure value. In this embodiment, the soft material used is not limited to flexible resin, rubber, silicone, or the like. Materials that can effectively transfer force are all within the scope of the present disclosure.

Optionally, in this embodiment, the housing of the wearable device may be arc-shaped, and the PT may be placed in the middle of the wearable device and is located at a center of a protrusion of the arc-shaped housing. When the housing of the wearable device contacts skin of a wrist to generate a pressure, the pressure can be effectively transferred to the PT. When the housing of the wearable device is designed as a non-arc-shaped plane, the soft material that fills a pressure transducer may appropriately protrude from the housing of the wearable device. When the housing of the wearable device contacts human skin, the pressure can be effectively transferred.

As shown in FIG. 4, when the wearable device performs the blood pressure measurement, a user may be guided to apply a pressure perpendicular to a contact surface between the wearable device and the human skin to the wearable device, so that a pressure is formed between the wearable device and the human skin (that is, a tested part). In this way, the collected PPG signal of the human skin has good quality. This is more helpful for measurement of a blood pressure value.

In this embodiment of this application, a plurality of possible implementations are provided based on quantities and layouts of the LEDs, the PDs, and the PTs.

In a possible implementation, 3 PDs, 3 LEDs, and 1 PT are arranged. The PT may be located in the center, and the LEDs and the PDs are spaced apart from each other around the PT. The LEDs and the PDs may be arranged around the PT at equal intervals, or may be arranged around the PT at unequal intervals. This is not limited in embodiments of this application.

Figure 5:
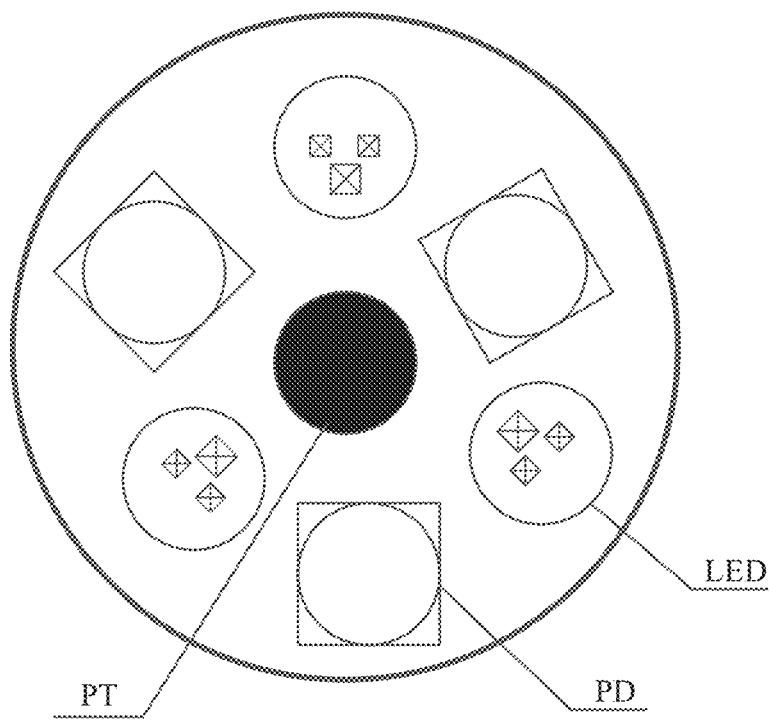
FIG. 5 is a top view of a wearable device according to an embodiment of this application.

For example, FIG. 5 is a top view of a wearable device. As shown in FIG. 5, a PT is located in a center, and 3 LEDs and 3 PDs are arranged around the PT at equal intervals.

In another possible implementation, 1 PD, 3 LEDs, and 3 PTs are arranged. The PD may be located in the center, and the LEDs and the PTs may be spaced apart from each other around the PD. In other words, the LEDs and the PTs are all distributed in a circular array.

Figure 6:
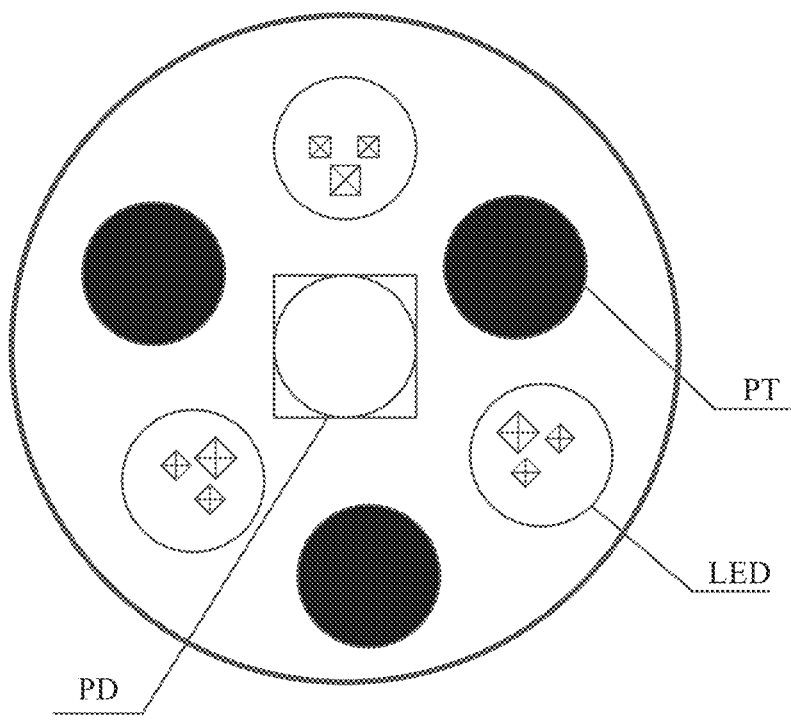
FIG. 6 is a top view of another wearable device according to an embodiment of this application.

For example, FIG. 6 is a schematic top view of a wearable device. As shown in FIG. 6, a PD is located in a center, and 3 LEDs and 3 PTs are all distributed in a circular array.

Through this implementation, when a housing of the wearable device contacts human skin, 3 pressure transducers may respectively measure pressure values. Based on a distribution of the pressure values, it may be determined whether the pressure is uniformly applied to the wearable device, thereby improving the measurement accuracy.

In still another possible implementation, 4 PDs, 4 LEDs, and 1 PT are arranged. The PT may be located in the center, and the LEDs and the PTs may be spaced apart from each other around the PT.

Figure 7:
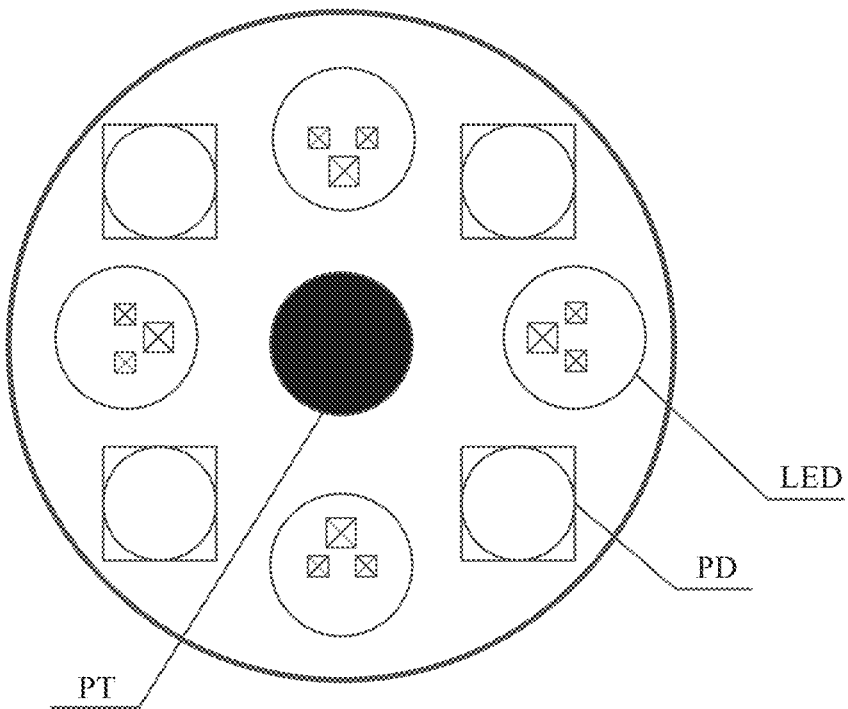
FIG. 7 is a top view of still another wearable device according to an embodiment of this application.

For example, FIG. 7 is a schematic top view of a wearable device. As shown in FIG. 7, a PT is located in a center, and 4 LEDs and 4 PDs are spaced apart from each other around the PT.

Through this implementation, a relatively large quantity of LEDs and PDs are provided. The relatively large quantity of PDs may collect more optical signals on the same optical path, and the collected optical signals are strong, which results in strong electrical signals generated therefrom and thus strong PPG signals, so as to improve quality of the PPG signal.

The structure of the wearable device provided in embodiments of this application is described in detail above, and the method provided in embodiments of this application is to be described in detail below.

It is to be noted that the method provided in embodiments of this application may be used for measuring not only the blood pressure, but also a heart rate, blood oxygen, and blood glucose, so as to improve accuracy of a measurement result.

Before the technical solutions of embodiments of this application are described, the following description is first given.

First, in embodiments of this application, terms such as "first" and "second" are used to distinguish between same or similar items with basically same functions and roles. A person skilled in the art may understand that the terms such as "first" and "second" do not limit a quantity or an execution order, and the terms such as "first" and "second" are not limited to be definitely different.

Second, in this application, a term such as "example" or "for example" is used to represent giving an example, an illustration, or a description. Any embodiment or design scheme described by using "example" or "for example" in this application is not to be explained as being preferred or advantageous over another embodiment or design scheme. Exactly, use of the term such as "example" or "for example" is intended to present a related concept in a specific manner.

Third, the term "at least one" means one or more, and "a plurality of" means two or more. The term "and/or" is used for describing an association relationship between associated objects and representing that three relationships may exist. For example, A and/or B may represent the following three cases: only A exists, both A and B exist, and only B exists, where A and B may be singular or plural. The character "/" generally indicates an "or" relationship between a preceding associated object and a latter associated object. "At least one of the following items (pieces)" or a similar expression thereof refers to any combination of these items, including any combination of singular items (pieces) or plural items (pieces). For example, at least one item (piece) of a, b, and c may represent: a, or b, or c, or a and b, or a and c, or b and c, or a, b, and c, where a, b, and c may be singular or plural.

Figure 8A:
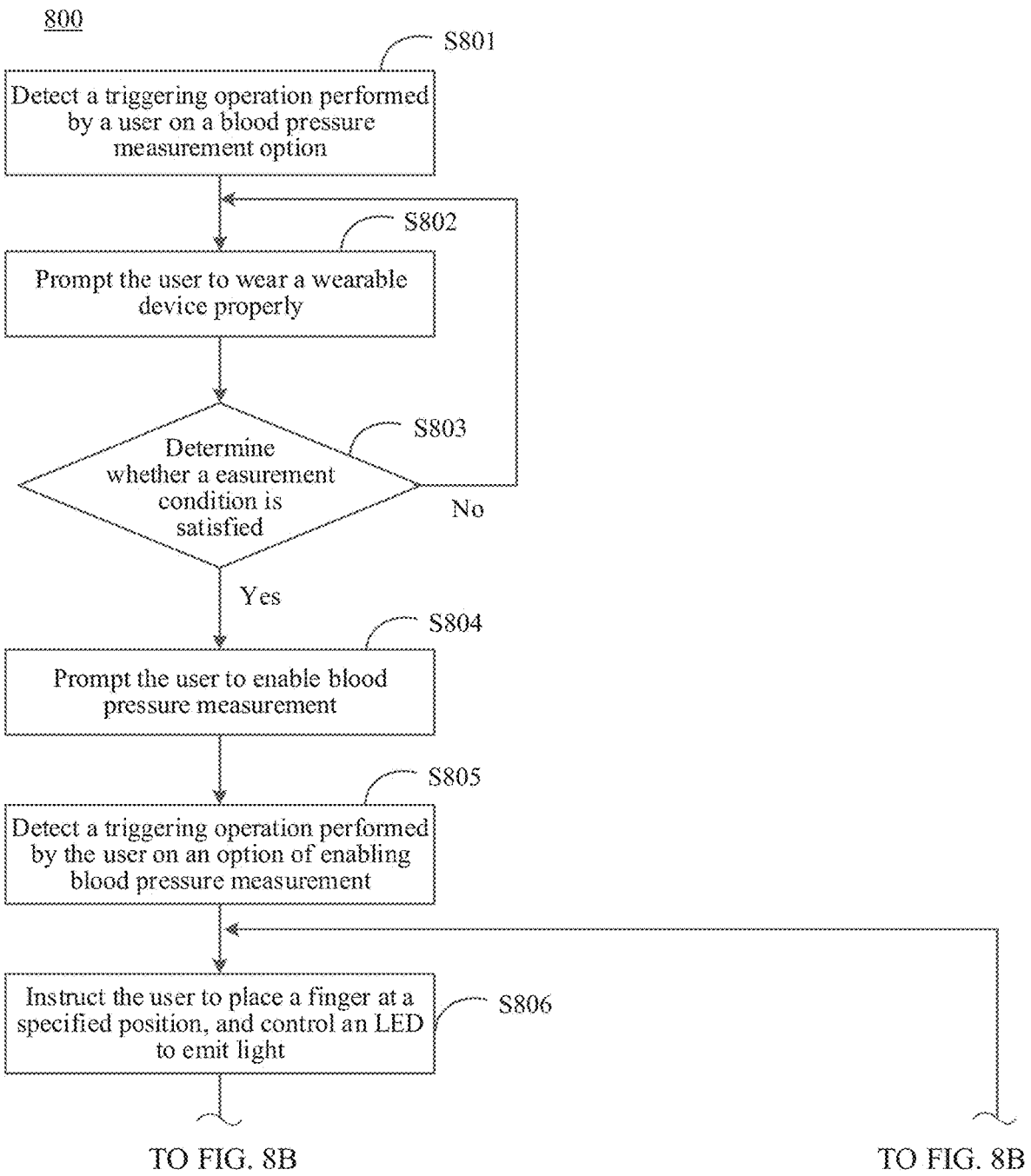
FIG. 8A and FIG. 8B are schematic flowcharts of a blood pressure measurement method for a wearable device according to an embodiment of this application.
Figure 8B:
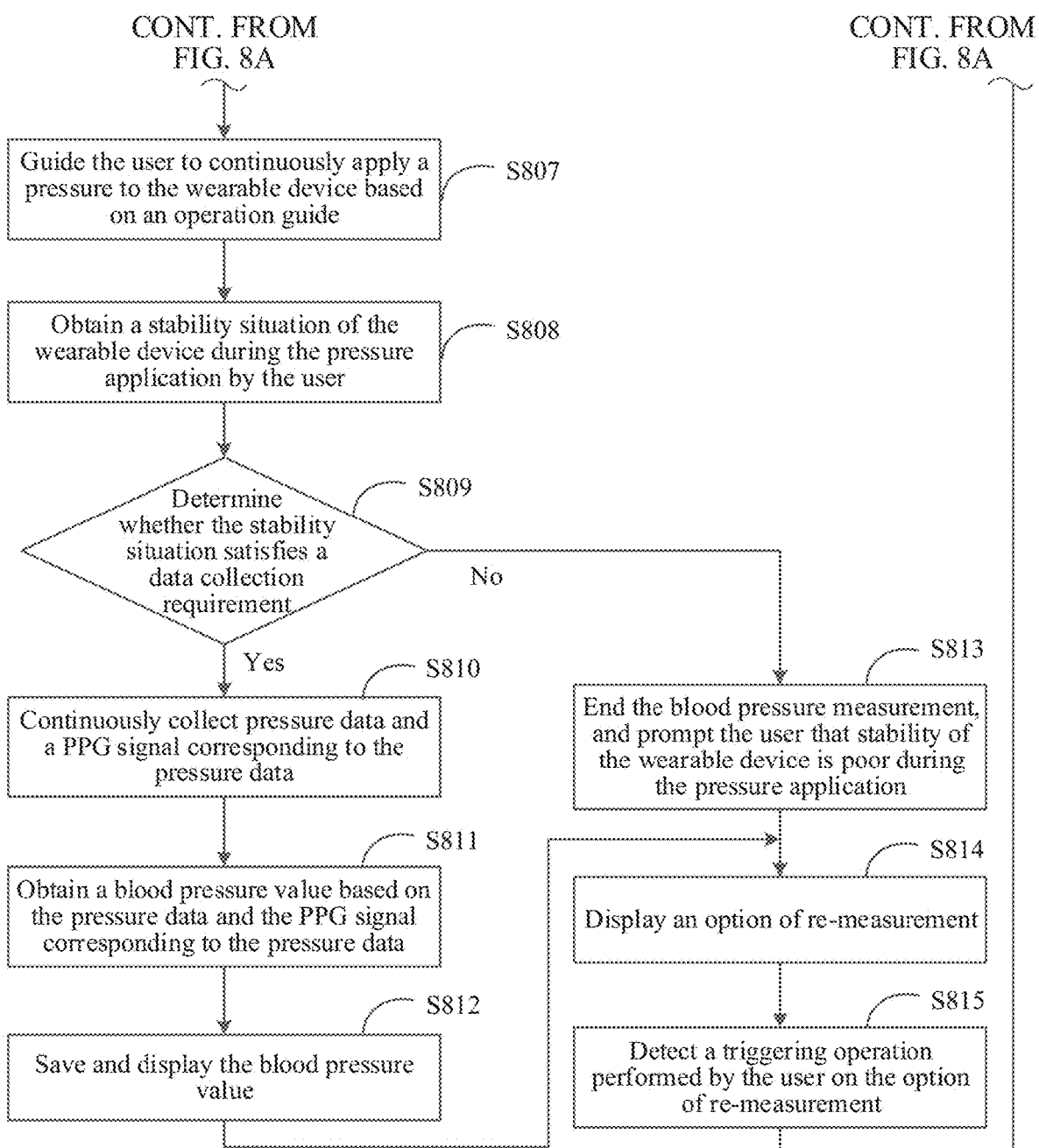

FIG. 8A and FIG. 8B are schematic flowcharts showing a blood pressure measurement method 800 for a wearable device. The method may be applicable to the scene shown in FIG. 1, but this embodiment of this application is not limited thereto. The method 800 may be performed by the wearable device, for example, the wearable device 102 shown in FIG. 1 above. A hardware structure diagram of the wearable device may be shown in FIG. 2, but this embodiment of this application is not limited thereto.

As shown in FIG. 8A and FIG. 8B, the method 800 may include the following steps.

S801: Detect a triggering operation performed by a user on a blood pressure measurement option.

The wearable device may display the blood pressure measurement option through a human-machine interaction interface, and the user may click the blood pressure measurement option to enter a blood pressure measurement interface. When the user clicks the blood pressure measurement option, the wearable device may detect the triggering operation performed by the user on the blood pressure measurement option. The user may also be referred to as a wearer. This is not limited in embodiments of this application.

S802: Prompt, in response to the triggering operation performed by the user on the blood pressure measurement option, the user to wear the wearable device properly.

The wearable device may prompt, by using sound and/or texts, the user to wear the wearable device properly. The prompt content may be "please wear the device straight and tightly". If the wearable device provides a prompt through the texts, the prompt content may be displayed on an interface. If the wearable device provides a prompt through the sound, the prompt content may be played through a speaker. If the wearable device provides a prompt through the sound and the texts, the prompt content may be played through the speaker and displayed through an interface.

The wearable device prompts the user to wear the wearable device properly before a test. This helps cause the wearable device to have good contact with skin, and helps improve quality of a collected PPG signal and then improve accuracy of blood pressure measurement.

S803: Determine whether a measurement condition is satisfied.

The wearable device determines whether the measurement condition is satisfied. In other words, the wearable device determines whether the blood pressure measurement may be performed in this case. If the measurement condition is satisfied, it may indicate that the blood pressure measurement may be effectively performed in a current state, and a blood pressure value has relatively high accuracy. If the measurement condition is not satisfied, it may indicate that the blood pressure measurement cannot be effectively performed in the current state, and the blood pressure value has relatively low accuracy.

The measurement condition may include at least one of the wearable device being in a relatively static state, the wearable device being in good contact with the skin, and the PPG signal having good quality.

The wearable device may obtain an acceleration of the wearable device through an ACC to determine whether the wearable device is in the relatively static state. The wearable device may obtain a pressure value through a PT to determine whether the wearable device is in good contact with the skin. The wearable device may determine, through the waveform feature of the PPG signal, whether the PPG signal has good quality. However, this embodiment of this application is not limited thereto.

Figure 9:
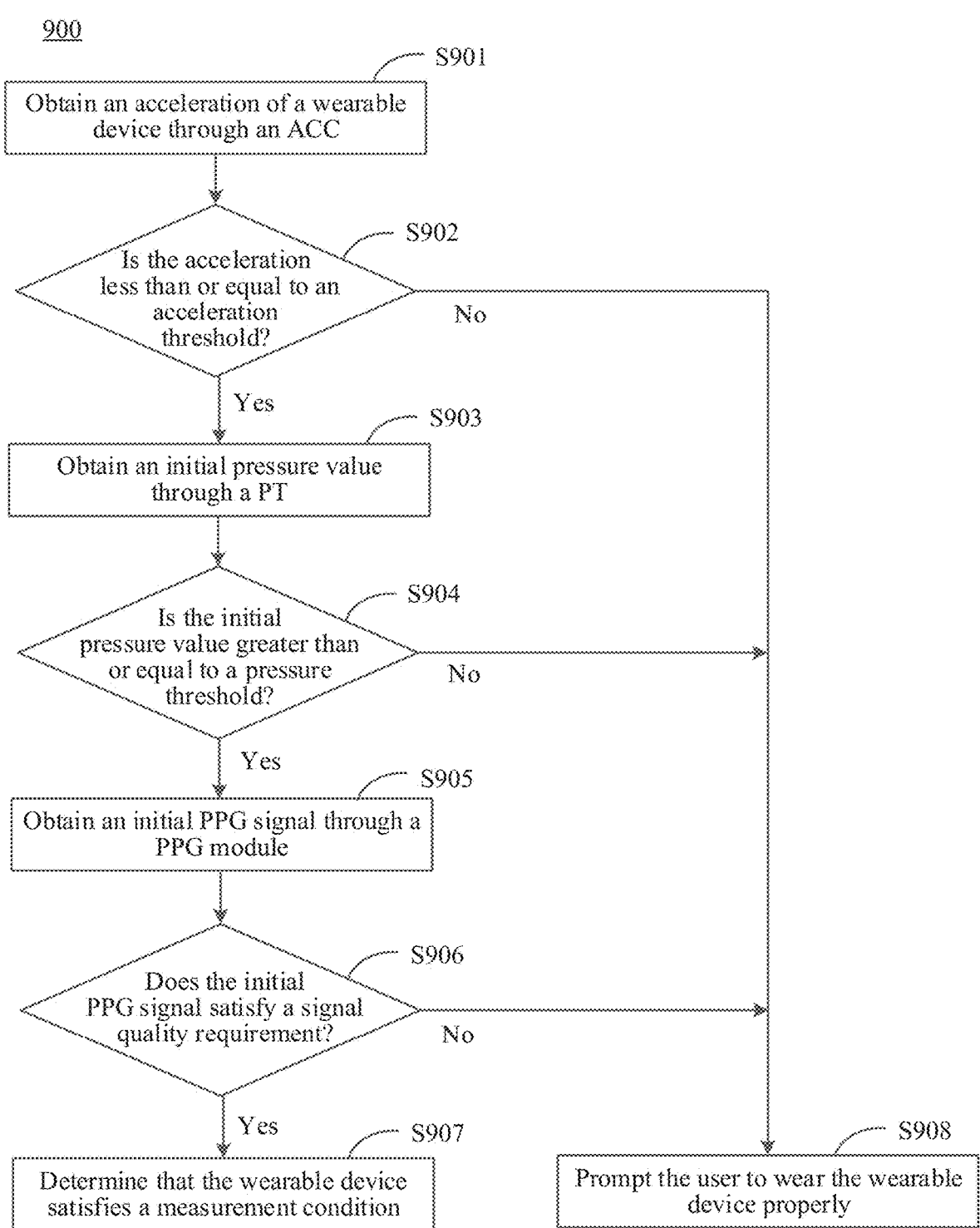
FIG. 9 is a schematic flowchart of a method for determining a measurement condition according to an embodiment of this application.

For example, the measurement condition may include that the wearable device is in a relatively static state, the wearable device is in good contact with the skin, and the PPG signal has good quality. FIG. 9 is a schematic flowchart showing a method 900 for determining a measurement condition. As shown in FIG. 9, the method 900 may include the following steps.

S901: Obtain an acceleration of a wearable device through an ACC.

The wearable device may obtain a signal of the ACC, and data carried by the signal is the acceleration of the wearable device.

S902: Determine whether the acceleration is less than or equal to an acceleration threshold.

The acceleration threshold is preset, and a specific value of the acceleration threshold is not limited in embodiments of this application.

If the acceleration is less than or equal to the acceleration threshold, it may indicate that the wearable device is in the relatively static state, and another condition may continue to be determined, that is, 903 is performed. If the acceleration is greater than the acceleration threshold, it may indicate that the wearable device is in a non-relatively static state or in a shaking state. A user may be prompted to wear the wearable device properly, that is, 908 is performed.

S903: Obtain an initial pressure value through a PT if the acceleration is less than or equal to the acceleration threshold.

The wearable device may obtain a signal of the PT, and data carried by the signal is a pressure value. The pressure value in this case may be referred to as the initial pressure value before blood pressure measurement starts, that is, before the user applies a pressure. It is to be understood that the initial pressure value is merely an example of a name. This is not limited in embodiments of this application.

S904: Determine whether the initial pressure value is greater than or equal to a pressure threshold.

The pressure threshold is preset, and a specific value of the pressure threshold is not limited in embodiments of this application.

If the initial pressure value is greater than or equal to the pressure threshold, it may indicate that the wearable device is in good contact with skin, that is, a wearing tightness is appropriate, and another condition may continue to be determined, that is, 905 is performed. If the initial pressure value is less than the pressure threshold, it may indicate that the wearable device is not in good contact with skin, that is, the wearable device is worn loosely, and the user may be prompted to wear the wearable device properly, that is, 908 is performed.

S905: Obtain an initial PPG signal through a PPG module if the initial pressure value is greater than or equal to the pressure threshold.

If the wearable device is in good contact with the skin, the wearable device may obtain a PPG signal in the state through the PPG module. The PPG signal in this case may be referred to as the initial PPG signal before the blood pressure measurement starts, that is, before the user applies a pressure. It is to be understood that the initial PPG signal is merely an example of a name. This is not limited in embodiments of this application.

A position where the PPG module is deployed may be referred to as a target position. In this embodiment of this application, the PT is added. The PT may also be deployed at the target position. A positional relationship between the PT and the PPG module is not limited in embodiments of this application.

S906: Determine whether the initial PPG signal satisfies a signal quality requirement.

The wearable device may determine in a plurality of manners whether the initial PPG signal satisfies the signal quality requirement.

In a possible implementation, it is determined, by using a waveform feature of the initial PPG signal, whether the signal quality requirement is satisfied.

For example, the wearable device may extract the waveform feature of the initial PPG signal through a feature extraction model, and compare the waveform feature of the initial PPG signal with a preset waveform feature, to determine whether the initial PPG signal satisfies the signal quality requirement.

Optionally, the wearable device may perform denoising and/or filtering on the initial PPG signal before extracting the waveform feature of the initial PPG signal, to ensure accuracy of the extracted waveform feature.

In another possible implementation, it is determined, by using waveform features of different optical signals, whether the initial PPG signal satisfies the signal quality requirement.

For example, the wearable device may use waveforms of a green light signal, a red light signal, and an infrared light signal to perform similarity or correlation comparison to determine whether the initial PPG signal satisfies the signal quality requirement.

If the initial PPG signal satisfies the signal quality requirement, it may indicate that the PPG signal has good quality. In other words, the wearable device satisfies the measurement condition, that is, S907 may be performed. If the initial PPG signal does not satisfy the signal quality requirement, it may indicate that the PPG signal has poor quality. The user may be prompted to wear the wearable device properly, that is, S908 is performed.

S907: It may be determined that the wearable device satisfies the measurement condition if the initial PPG signal satisfies the signal quality requirement.

The wearable device may determine that the wearable device satisfies the measurement condition when the wearable device satisfies the following conditions:

the acceleration is less than or equal to the acceleration threshold; the initial pressure value is greater than or equal to the pressure threshold; and the initial PPG signal satisfies the signal quality requirement.

S908: Prompt the user to wear the wearable device properly.

The wearable device may determine that the wearable device does not satisfy the measurement condition and the user is prompted to wear the wearable device properly when the wearable device satisfies at least one of the following conditions:

the acceleration is greater than the acceleration threshold; the initial pressure value is less than the pressure threshold; or the initial PPG signal does not satisfy the signal quality requirement.

It is to be noted that an execution order of S902, S904, and S906 described above is not limited in embodiments of this application.

If the wearable device satisfies the measurement condition, the blood pressure measurement may be performed, that is, S804 is performed. If the wearable device does not satisfy the measurement condition, the user may be continuously prompted to wear the wearable device properly, that is, S802 is performed.

S804: Prompt the user to enable blood pressure measurement if the measurement condition is satisfied.

The wearable device may prompt, by using sound and/or texts, the user to wear the wearable device properly. A prompt content may be "please start the blood pressure measurement". If the wearable device provides a prompt through the texts, the prompt content may be displayed on an interface. If the wearable device provides a prompt through the sound, the prompt content may be played through a speaker. If the wearable device provides a prompt through the sound and the texts, the prompt content may be played through the speaker and displayed through an interface.

S805: Detect a triggering operation performed by a user on an option of enabling blood pressure measurement.

The option of enabling blood pressure measurement may also be referred to as an option of starting blood pressure measurement. This is not limited in embodiments of this application.

The wearable device may enable the blood pressure measurement option through the human-machine interaction interface, and the user may click the option of enabling blood pressure measurement to enable blood pressure measurement. When the user clicks the option of enabling blood pressure measurement, the wearable device may perform the blood pressure measurement.

S806: Instruct the user to place a finger at a specified position, and control an LED to emit light.

The wearable device may prompt, through the texts or the sound, the user to place the finger at the specified position. The specified position may be a center of a screen of the wearable device, or may be an upper side and a lower side or a left side and a right side of the screen of the wearable device. This is not limited in embodiments of this application. If the specified position is the center of the screen of the wearable device, the wearable device may instruct the user to press the center of the screen with one finger. The prompt content may be "please press the center of the screen with the index finger", but this embodiment of this application is not limited thereto. If the specified position is the upper side and the lower side of the screen of the wearable device, the wearable device may instruct the user to respectively press the upper side and the lower side of the screen with two fingers. The prompt content may be "please press the upper side of the screen with the index finger and the bottom of the screen with the thumb", but this embodiment of this application is not limited thereto.

The wearable device may also control the LED to emit an optical signal to obtain a PPG signal for the blood pressure measurement.

S807: Guide the user to continuously apply a pressure to the wearable device based on an operation guide.

The wearable device may guide the user to continuously apply a pressure to the wearable device through texts, sound, an image, or a color. In other words, the operation guide may be the texts, the sound, the image, or the color. This is not limited in embodiments of this application. In a possible implementation, the operation guide may be "please increase the pressing pressure". The wearable device may guide the user through the sound and/or the texts. In another possible implementation, the wearable device displays a pressure curve through the human-machine interaction interface, and guides the user to continuously apply the pressure to the wearable device based on the pressure curve.

The wearable device may guide the user to continuously apply the pressure to the wearable device over a period of time based on the operation guide. The continuously applied pressure is perpendicular to a tested part (for example, a wrist), so that a continuous pressure change is generated between the wearable device and the tested part. A duration of the continuous pressure application is not limited in embodiments of this application. In a possible implementation, the duration of the continuous pressure application may be 30 seconds.

It is to be noted that the process of continuous pressure application is a process of increasing the pressure. In this embodiment of this application, blood vessels in the skin in contact with the wearable device are squeezed through the continuous pressure application by the user, so as to measure the blood pressure.

S808: Obtain a stability situation of the wearable device during the pressure application by the user.

On one hand, to prevent the wearable device in a shaking state during the pressure application from affecting collection of data and accuracy of the blood pressure value, the wearable device obtains the stability situation of the wearable device during the pressure application by the user.

For example, the wearable device may obtain the acceleration of the wearable device through the ACC to determine whether the wearable device is in the shaking state.

On the other hand, to prevent the wearable device from being skewed or warped and affecting collection of data and accuracy of the blood pressure value as a result of uneven pressure application by the user during the pressure application, the wearable device obtains the stability situation of the wearable device during the pressure application by the user.

For example, the wearable device may obtain an angular velocity of the wearable device through a gyroscope to determine whether the wearable device is in a skewed or warped state.

S809: Determine whether the stability situation satisfies a data collection requirement.

During the pressure application, if the wearable device is in the shaking state or in the skewed or warped state, the pressure data and the PPG signal are inaccurate, and the collection of the data is affected. If the wearable device is in a non-shaking state or in a non-skewed or non-warped state, the pressure data and the PPG signal are relatively accurate, and data collection may be performed. In other words, the data collection requirement is satisfied.

The wearable device determines whether the stability situation satisfies the data collection requirement. In other words, the wearable device determines whether the wearable device is in the shaking state or in the skewed or warped state during the pressure application.

If the stability situation of the wearable device satisfies the data collection requirement during the pressure application by the user, the data collection may be performed, that is, S810 is performed. If the stability situation of the wearable device does not satisfy the data collection requirement during the pressure application by the user, the blood pressure measurement may be ended, that is, S813 is performed.

S810: Continuously collect the pressure data and the PPG signal corresponding to the pressure data if the stability situation satisfies the data collection requirement.

If the stability situation satisfies the data collection requirement, the wearable device may continuously collect the pressure data and the PPG signal corresponding to the pressure data. In other words, during the pressure application by the user, the wearable device may collect a plurality of pieces of pressure data and simultaneously collect a PPG signal corresponding to each piece of pressure data. n pieces of pressure data may be collected, where n is an integer greater than or equal to 2.

Optionally, the wearable device may display a waveform of the PPG signal in real time on a display interface.

S811: Obtain the blood pressure value based on the pressure data and the PPG signal corresponding to the pressure data.

During the pressure application by the user, the pressure increases as the pressure application process progresses. Different pressure values correspond to different PPG signals. The wearable device may obtain the blood pressure value based on the plurality of pieces of pressure data and the PPG signal corresponding to each piece of pressure data.

For example, FIG. 10 is a schematic flowchart showing a method 1000 for calculating a blood pressure value. As shown in FIG. 10, the method 1000 may include the following steps.

S1001: Obtain a $1^{st}$ pressure value to an $n^{th}$ pressure value during continuous pressing by a user.

During the pressure application by the user, a pressure increases as a pressure application process progresses. The $1^{st}$ pressure value is the smallest one of the n pressure values, and the $n^{th}$ pressure value is the largest one of the n pressure values. A value of n may be 3, or may be 5, and may also be 10. This is not limited in embodiments of this application. The $1^{st}$ pressure value to the $n^{th}$ pressure value may also be referred to as a plurality of pressure values. This is not limited in embodiments of this application.

S1002: Obtain a PPG signal corresponding to each pressure value.

A wearable device may also obtain the PPG signal under the pressure value while obtaining the $1^{st}$ pressure value. In other words, the wearable device controls an LED to emit light, receives a reflected optical signal through a PD, converts the reflected optical signal into an electrical signal, and then converts the electrical signal into the PPG signal for blood pressure measurement. By analogy, the wearable device may obtain the PPG signal corresponding to each pressure value, and then obtain n PPG signals. The n PPG signals may also be referred to as a plurality of PPG signals. This is not limited in embodiments of this application.

Different pressure values correspond to different PPG signals, and waveforms of the PPG signals under different pressure values are different. When the pressure value is relatively small, the PPG signal is relatively weak, and a pulse pulsation amplitude of a waveform of the PPG signal is relatively small. As the pressure gradually increases, the optical signal emitted by the LED may be more effectively incident on a tested part, the PD may receive increasingly more optical signals reflected from the tested part, and the pulse pulsation amplitude of the waveform of the PPG signal is increasingly great and maximized. Afterward, as the pressure gradually increases, the pressure affects pulsation of blood vessels in the tested part, causing a pulsation magnitude to be constantly limited and form vascular occlusion. The pulse pulsation amplitude of the waveform of the PPG signal gradually decreases until a waveform curve becomes straight and has no pulse shape. In this embodiment of this application, the pressure applied by the user may cause the pulse pulsation amplitude of the waveform of the PPG signal to change from a small value to a large value until a maximum value, and then from the large value to the small value until the waveform curve becomes straight.

Figure 11:
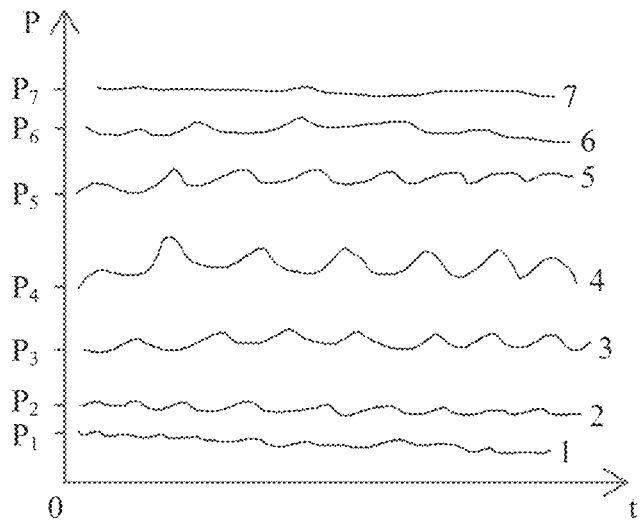
FIG. 11 is a schematic diagram of waveform curve changes of a PPG signal according to an embodiment of this application.

For example, FIG. 11 is a schematic diagram showing waveform curve changes of a PPG signal. As shown in FIG. 11, n is equal to 7. When n=1, a pressure value is $P_1$. When n=2, the pressure value is $P_2$. When n=3, the pressure value is $P_3$. When n=4, the pressure value is $P_4$. When n=5, the pressure value is $P_5$. When n=6, the pressure value is $P_6$. When n=7, the pressure value is $P_7$. $P_1<P_2<P_3<P_4<P_5<P_6<P_7$. At a pressure value ($P_1$, $P_2$, $P_3$, $P_4$, $P_5$, $P_6$, or $P_7$), the waveform of the PPG signal constantly changes with time. As the pressure value continuously increases, that is, from $P_1$ to $P_7$, the pulse pulsation amplitude of the waveform of the PPG signal changes from a small value to a large value until a maximum value, and then from the large value to the small value until the waveform curve becomes straight. It may be seen from FIG. 11 that the pulse pulsation amplitude of the waveform of the PPG signal corresponding to a $4^{th}$ pressure value is the largest. The waveform curve of the PPG signal corresponding to a $7^{th}$ pressure value is straight and has no pulse shape.

S1003: Extract a waveform feature of each PPG signal.

The wearable device may extract the waveform feature of each PPG signal through a feature extraction model. The waveform form of each PPG signal includes a physiological feature of a human body. The waveform feature of each PPG signal may include at least one of a main peak height of a PPG waveform, a height of a dicrotic notch, an amplitude height of a replay wave, a pulse conduction time, diastole, systole, and rise time and fall time of the waveform.

Figure 12:
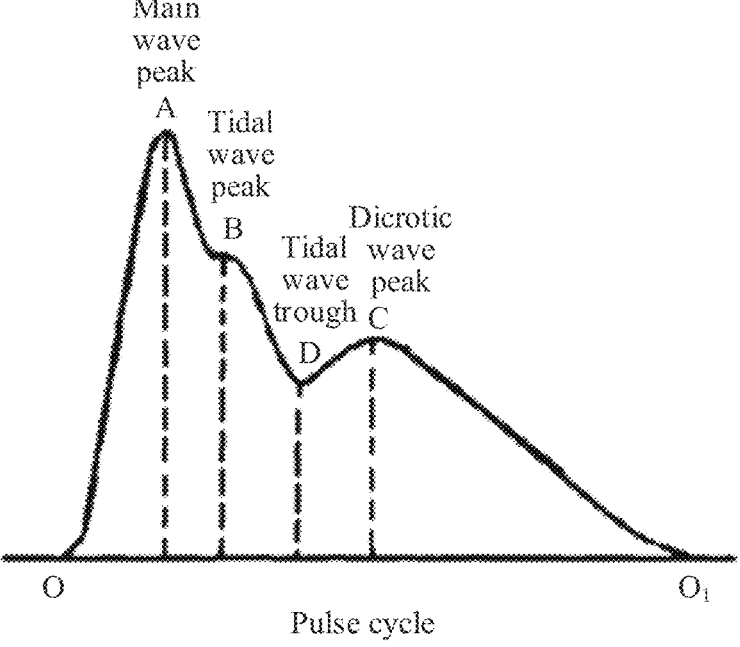
FIG. 12 is a schematic diagram of a waveform of a PPG signal according to an embodiment of this application.

For example, FIG. 12 is a schematic diagram showing a waveform of a PPG signal. As shown in FIG. 12, the waveform of the PPG signal is described by using one pulse cycle as an example. A point O is a starting point of a cardiac ejection phase. A point A is a highest point of an aortic pressure and reflects the maximum pressure and volume in the artery. A point B is a stopping point of left ventricular ejection, is a peak point of a reflection wave and also referred to as a tidal wave peak, and reflects a magnitude of tension, compliance, and peripheral resistance of the artery. A point D is a tidal wave trough point, that is, a boundary point between cardiac contraction and relaxation, and mainly reflects the magnitude of the peripheral resistance.

An OA segment waveform is an ascending branch of the pulse waveform, which is caused by expansion of a vascular wall as a result of left ventricular ejection and a rapid rise of arterial blood pressure during sudden expansion of an arterial wall. A cardiac output, an ejection velocity, and a resistance are main factors affecting the amplitude and a slope of the ascending branch, which are generally expressed by a slope and an amplitude of rising of a pulse wave waveform. A larger cardiac output, a faster ejection velocity, higher aortic elasticity, and smaller resistance lead to a larger slope and a higher amplitude. On the contrary, the slope is relatively small, and the amplitude is relatively low. An AD segment waveform is an anterior segment of a descending branch, which is caused by a process in which the ejection velocity begins to decrease in a later stage of the ventricular ejection, causing blood flow around the aorta to be greater than blood flow into the aorta, the aorta changes from expansion to retraction, and the arterial blood pressure gradually decreases. A $DO_1$ segment waveform is a posterior segment of the descending branch, also referred to as a dicrotic wave, which is formed by ventricular dilation, a continuous decrease in the arterial blood pressure, and reflux of blood in the aorta to a ventricle. This reflects a functional status of the aorta, vascular elasticity, and a blood flow state.

The wearable device may extract waveform features such as the main peak height of the waveform of the PPG signal, the height of the dicrotic notch, the amplitude height of the replay wave, the pulse conduction time, the diastole, the systole, and the rise time and fall time of the waveform.

S1004: Determine, from n PPG signals, a PPG signal that does not have a waveform feature, where the PPG signal is an $i^{th}$ signal.

The wearable device may determine, from the n PPG signals based on the waveform feature of each PPG signal, the PPG signal that does not have a waveform feature. The PPG signal that does not have a waveform feature is an $i^{th}$ PPG signal, where i is greater than or equal to 1, and i is less than or equal to n. The PPG signal that does not have a waveform feature may also be referred to as a first PPG signal whose waveform feature is less than or equal to a preset waveform feature. This is not limited in embodiments of this application.

For example, in the foregoing example shown in FIG. 11, a $7^{th}$ PPG signal is the PPG signal that does not have a waveform feature, where i=7.

S1005: Determine a pressure value corresponding to the PPG signal that does not have a waveform feature as a systolic blood pressure (SBP).

The pressure value corresponding to the PPG signal that does not have a waveform feature is an $i^{th}$ pressure value, and the wearable device may determine the $i^{th}$ pressure value as the systolic blood pressure.

For example, in the foregoing example shown in FIG. 11, the $7^{th}$ PPG signal is the PPG signal that does not have a waveform feature, where i=7. The wearable device may determine the $7^{th}$ pressure value as the systolic blood pressure.

S1006: Input the $1^{st}$ pressure value to the $i^{th}$ pressure value and the waveform feature of the PPG signal corresponding to each pressure value into a neural network model 1, to obtain a diastolic blood pressure (DBP).

The wearable device may input the $1^{st}$ pressure value and the waveform feature of the PPG signal corresponding to the $1^{st}$ pressure value to the $i^{th}$ pressure value and the waveform feature of the PPG signal corresponding to the $i^{th}$ pressure value into the neural network model 1, to obtain the DBP.

It is to be noted that input to the neural network model 1 is the pressure value and the waveform feature of the PPG signal corresponding to the pressure value, and output of the neural network model is the DBP. The neural network model 1 may be trained by using a large quantity of historical data. The neural network model 1 may also be referred to as a first neural network model. This is not limited in embodiments of this application.

According to the method 1000, the SBP (that is, a high pressure) of the blood pressure may be directly measured through the PT, and the DBP (that is, a low pressure) is calculated through the waveform feature presented by the PPG signal. Compared with the blood pressure value calculated through regression or another calculation method, accuracy of the blood pressure value is improved.

After the blood pressure value is obtained through the method 1000, the wearable device may continue to perform S812. It is to be noted that the method 1000 is merely a specific implementation of obtaining the blood pressure value. This embodiment of this application is not limited thereto.

S812: Save and display the blood pressure value.

The blood pressure value includes the SBP and the DBP. The wearable device may save the blood pressure value, and may also save a test time of the blood pressure value.

The wearable device may also display the blood pressure value on an interface.

Figure 13:
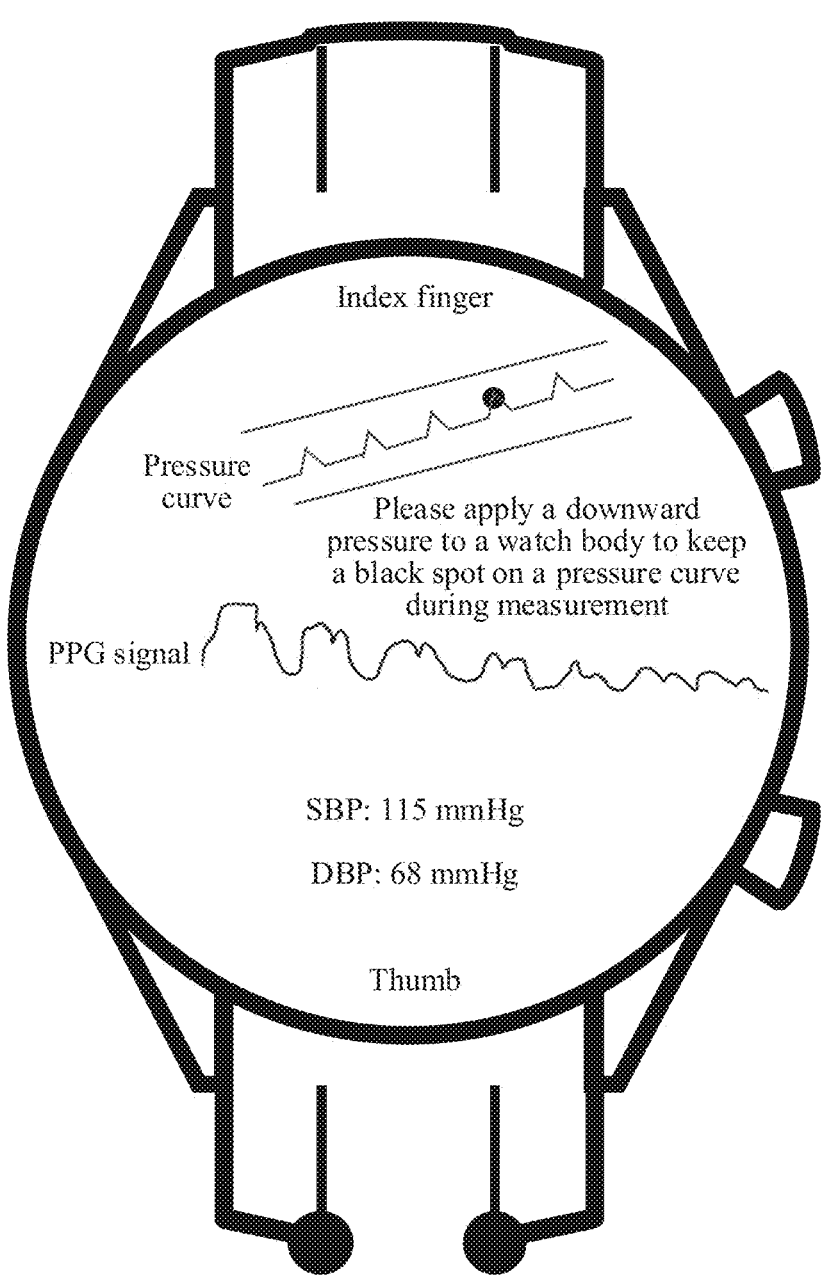
FIG. 13 is a schematic diagram of a blood pressure measurement interface according to an embodiment of this application.

For example, the wearable device may display the measured blood pressure value on the interface, may also display a pressure curve on the interface to guide the user to continuously apply the pressure based on the pressure curve, and may also display the waveform of the PPG signal. FIG. 13 is a schematic diagram showing a blood pressure measurement interface. As shown in FIG. 13, a wearable device may guide a user to continuously apply a pressure to the wearable device for 10 seconds with a thumb and an index finger in a text (the thumb and the index finger) display position, guide the user to continuously apply the pressure to the wearable device through texts "please apply a downward pressure to a watch body to keep a black spot on a pressure curve during measurement", and display upper and lower limits of the pressure curve on an interface to regulate a behavior of applying the pressure by the user. In addition, during the pressure application by the user, a prompting mode such as a color or sound may also be displayed on the interface, to guide the user to correctly apply the pressure and ensure the measurement requirement. In other words, during the measurement, application of the downward pressure is to be maintained to avoid a measurement error caused by skewness or warpage of the wearable device. A position of the thumb may be referred to as a first position, and a position of the index finger may be referred to as a second position. This is not limited in embodiments of this application. The position of the thumb and the position of the index finger may be collectively referred to as a pressing position. The texts "please apply a downward pressure to a watch body to keep a black spot on a pressure curve during measurement" may be referred to as prompt information. The interface shown in FIG. 13 may be referred to as a first interface. This is not limited in embodiments of this application.

During the pressure application by the user, the wearable device collects pressure data, obtains a PPG signal under the pressure data, and displays a waveform of the PPG signal on the interface. When the wearable device determines an SBP and a DBP according to the foregoing method 1000, a blood pressure value is displayed on the interface, that is, SBP: 115 millimetres of mercury (millimetre of mercury, mmHg), and DBP: 68 mmHg.

The wearable device may wait for an operation performed by the user after displaying the blood pressure value, or may display an option of re-measurement to re-measure the blood pressure, and may also display an option of quitting to end blood pressure measurement.

S813: End the blood pressure measurement and prompt the user that stability of the wearable device is poor in the process if a stability situation does not satisfy a calculation requirement.

If the stability situation of the wearable device does not satisfy a data collection requirement during the pressure application by the user, the blood pressure measurement may be ended, and the user may be prompted with texts or sound that the stability of the wearable device is poor.

S814: Display the option of re-measurement.

The wearable device may also display the option of re-measurement through the human-machine interaction interface, so as to facilitate re-measurement by the user.

S815: Detect a triggering operation performed by the user on the option of re-measurement.

When the wearable device detects the triggering operation performed by the user on the option of re-measurement, S806-S812 described above may be performed.

According to the blood pressure measurement method for a wearable device provided in embodiments of this application, it is determined whether the measurement condition is satisfied before the blood pressure measurement is performed. Measurement is performed based on the measurement condition that is satisfied, which helps improve accuracy of the blood pressure value. The user is guided to apply the pressure after the blood pressure measurement is enabled, which helps improve user experience, and a tested part is in a relaxed state, which helps ensure accuracy of the blood pressure value. During the pressure application by the user, the stability situation of the wearable device also needs to be determined, which helps ensure accuracy of data collection, thereby improving the accuracy of the blood pressure value.

According to the foregoing blood pressure measurement method for a wearable device, the user needs to measure blood pressure, and the wearable device measures the blood pressure based on the operation performed by the user. An embodiment of this application further provides a blood pressure measurement method for a wearable device, so as to automatically measure blood pressure of a user.

Figure 14B:
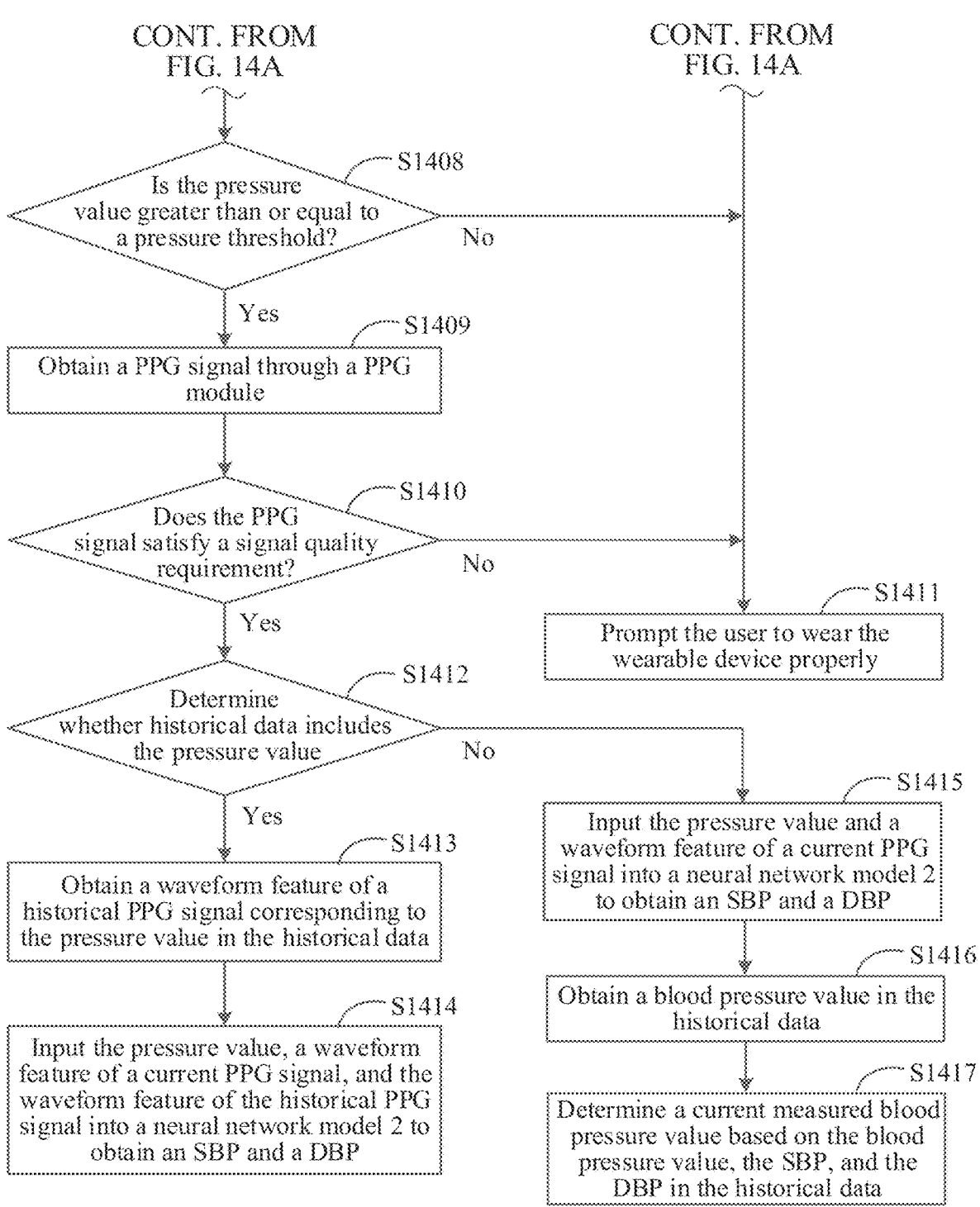

For example, FIG. 14A and FIG. 14B are schematic flowcharts showing a blood pressure measurement method 1400 for a wearable device. As shown in FIG. 14A and FIG. 14B, the method 1400 may include the following steps.

S1401: Detect a triggering operation performed by a user on an automatic blood pressure measurement option.

The wearable device may display the automatic blood pressure measurement option through a human-machine interaction interface. When the triggering operation performed by the user on the automatic blood pressure measurement option is detected, the wearable device may periodically measure blood pressure of the user based on a preset period until the user disables the automatic blood pressure measurement option.

Optionally, the wearable device may also provide the user with an option of setting a measurement time through the human-machine interaction interface. The user may flexibly set a blood pressure measurement time. When the wearable device detects the triggering operation performed by the user on the automatic blood pressure measurement option, the blood pressure of the user may be measured at the blood pressure measurement time set by the user.

S1402: Determine whether a measurement time is reached.

The measurement time may be a preset measurement time, or may be a measurement time set by the user. This is not limited in embodiments of this application. The preset measurement time may be periodic or aperiodic. This is not limited in embodiments of this application.

For example, if the preset measurement time is 5 p.m. on Tuesday and 5 p.m. on Friday every week, the wearable device may determine in real time whether the measurement time is 5 p.m. on Tuesday or 5 p.m. on Friday.

If the wearable device detects that the measurement time is reached, to ensure accuracy of blood pressure measurement, it may be determined whether a condition for the blood pressure measurement is satisfied, that is, S1403 may be performed. If the wearable device detects that the measurement time is not reached, the detection may be continued, that is, S1402 may be performed.

S1403: Obtain an acceleration of the wearable device through an ACC if the measurement time is reached.

For the step, reference may be made to S901 described above. Details are not described herein again.

S1404: Determine whether the acceleration is less than or equal to an acceleration threshold.

For the step, reference may be made to S902 described above. Details are not described herein again.

S1405: Obtain an angular velocity of the wearable device through a gyroscope if the acceleration is less than or equal to the acceleration threshold.

The wearable device may determine a wearing state of the wearable device through a signal of the gyroscope, that is, may determine whether the wearable device is worn straight. In other words, it may be determined whether the wearable device is worn askew.

The angular velocity of the wearable device may include an angular velocity in a horizontal direction and/or an angular velocity in a vertical direction. This is not limited in embodiments of this application.

S1406: Determine whether the angular velocity is less than or equal to an angular velocity threshold.

The angular velocity threshold is preset, and a specific value of the angular velocity threshold is not limited in embodiments of this application.

If the angular velocity is less than or equal to the angular velocity threshold, it may indicate that the wearable device is worn straight, or it may indicate that the wearable device is not worn askew. If the angular velocity is greater than the angular velocity threshold, it may indicate that the wearable device is not worn straight, or it may indicate that the wearable device is worn askew.

S1407: Obtain a pressure value through a PT if the angular velocity is less than or equal to the angular velocity threshold.

For the step, reference may be made to S903 described above. Details are not described herein again.

S1408: Determine whether the pressure value is greater than or equal to a pressure threshold.

For the step, reference may be made to S904 described above. Details are not described herein again.

S1409: Obtain an initial PPG signal through a PPG module if the pressure value is greater than or equal to the pressure threshold.

For the step, reference may be made to S905 described above. Details are not described herein again.

S1410: Determine whether a PPG signal satisfies a signal quality requirement.

For the step, reference may be made to S906 described above. Details are not described herein again.

S1411: Prompt the user to wear the wearable device properly.

The wearable device may determine that the wearable device does not satisfy the condition for the blood pressure measurement and the user is prompted to wear the wearable device properly when the wearable device satisfies at least one of the following conditions:

the acceleration is greater than the acceleration threshold; the angular velocity is greater than the angular velocity threshold; the pressure value is less than the pressure threshold; or the PPG signal does not satisfy the signal quality requirement.

It is to be noted that an execution order of S1404, S1406, S1408, and S14010 described above is not limited in embodiments of this application.

S1412: Determine whether historical data includes the foregoing pressure value if the PPG signal satisfies the signal quality requirement.

The wearable device may determine that the wearable device may perform the blood pressure measurement when the wearable device satisfies the following conditions:

the acceleration is less than or equal to the acceleration threshold; the angular velocity is less than or equal to the angular velocity threshold; the pressure value is greater than or equal to the pressure threshold; and the initial PPG signal satisfies the signal quality requirement.

The historical data is data generated during a previous blood pressure measurement. For example, the historical data may include a historically obtained pressure value, a waveform feature of the PPG signal corresponding to each pressure value, and a historically measured blood pressure value. The historical data may include data generated during a plurality of blood pressure measurements, or may include only data generated during the previous blood pressure measurement. This is not limited in embodiments of this application.

If the historical data includes the foregoing pressure value, the waveform feature of the PPG signal corresponding to the pressure value may be obtained, that is, S1413 may be performed. If the historical data does not include the foregoing pressure value, the blood pressure value may be determined by using the pressure value and the waveform feature of the PPG signal corresponding to the pressure value, that is, S1415 is performed.

S1413: Obtain a waveform feature of a historical PPG signal corresponding to the pressure value in the historical data if the historical data includes the foregoing pressure value.

If the historical data includes the foregoing pressure value, the historical data may include the waveform feature of the historical PPG signal corresponding to the pressure value.

S1414: Input the pressure value, a waveform feature of a current PPG signal, and the waveform feature of the historical PPG signal into a neural network model 2 to obtain an SBP and a DBP.

A main peak of the waveform of the PPG signal corresponds to the SBP, and a replay wave peak corresponds to the DBP. The wearable device may determine the SBP and the DBP based on the pressure value and the waveform feature of the PPG signal. The wearable device may input the foregoing pressure value, the waveform feature of the current PPG signal, and the waveform feature of the historical PPG signal into the neural network model 2, to obtain the SBP and the DBP.

It is to be noted that the input to the neural network model 2 is the pressure value and the waveform feature corresponding to the pressure value, and output of the neural network model is the SBP and the DBP. The neural network model 2 may be trained by using a large quantity of historical data. It may be understood that the neural network model 2 may be the same as or different from the foregoing neural network model 1. If the neural network model 1 is the same as the foregoing neural network model 2, the foregoing neural network model 1 may also output the SBP and the DBP in the blood pressure value. However, only the DBP is used in the foregoing solution.

Through such an implementation, the waveform feature of the historical PPG signal is increased. More features corresponding to a same pressure value indicate a more accurate SBP and a more accurate DBP that are obtained, so that accuracy of the blood pressure value may be improved.

S1415: Input the pressure value and the waveform feature of the current PPG signal into the neural network model 2 to obtain the SBP and the DBP if the historical data does not include the foregoing pressure value.

If the historical data does not include the foregoing pressure value, the waveform feature of the PPG signal included in the historical data cannot be used. The wearable device may input the pressure value and the waveform feature of the current PPG signal into the neural network model 2 to obtain the SBP and the DBP. The neural network model 2 may also be referred to as a second neural network model. This is not limited in embodiments of this application.

To prevent an inaccurate blood pressure value obtained by using only one blood pressure value and the waveform feature of the PPG signal corresponding to the blood pressure value, the wearable device may also perform S1416.

S1416: Obtain the blood pressure value in the historical data.

S1417: Determine a current measured blood pressure value based on the blood pressure value, the SBP, and the DBP in the historical data.

The SBP and the DBP may be referred to as temporary blood pressure values.

The wearable device may obtain the blood pressure value in the historical data, and use the blood pressure value in the historical data and the temporary blood pressure values (that is, the SBP and the DBP) to determine a current blood pressure value, to improve accuracy of the blood pressure value.

For example, the blood pressure value in the historical data may have different weight coefficients. A sum of the weight coefficients of the temporary blood pressure values and a weight coefficient of the historical blood pressure value is 1. The current measured blood pressure value may be a sum of the historical blood pressure value and a corresponding weight coefficient thereof plus a sum of the temporary blood pressure value and a corresponding weight coefficient thereof.

Optionally, the wearable device may also obtain a previous blood pressure value in the historical data, and compares the previous blood pressure value with the current blood pressure value. If a great difference exists between the blood pressure values, it may be considered that the current blood pressure value is inaccurate and may be discarded, or the weight coefficient is reduced.

According to the blood pressure measurement method for a wearable device provided in this embodiment of this application, the blood pressure may be automatically measured, and before the blood pressure is automatically measured, a state of motion of the wearable device and a contact situation between the wearable device and the tested part are detected, and detections as to whether the wearable device is skewed and warped and whether the PPG signal has good quality are performed. The blood pressure measurement is performed in a good state, which helps improve accuracy of the blood pressure. The method further provides different methods for measuring a blood pressure value based on different situations, which is flexible. When a current measured pressure value does not exist in the historical data, the historical blood pressure value may be used for calculation, so as to improve the accuracy of the blood pressure value. When the current measured pressure value exists in the historical data, the waveform feature of the historical PPG signal may be used for calculating the blood pressure value, so as to improve the accuracy of the blood pressure value.

The sequence number of the foregoing processes does not mean the order of execution, and the order of execution of each process is to be determined by the function and internal logic thereof, and is not to constitute any limitation on the implementation process of embodiments of this application.

The method provided in embodiments of this application is described in detail with reference to FIG. 1 to FIG. 14A and FIG. 14B above, and a device provided in embodiments of this application is to be described in detail with reference to FIG. 15 and FIG. 16.

Figure 15:
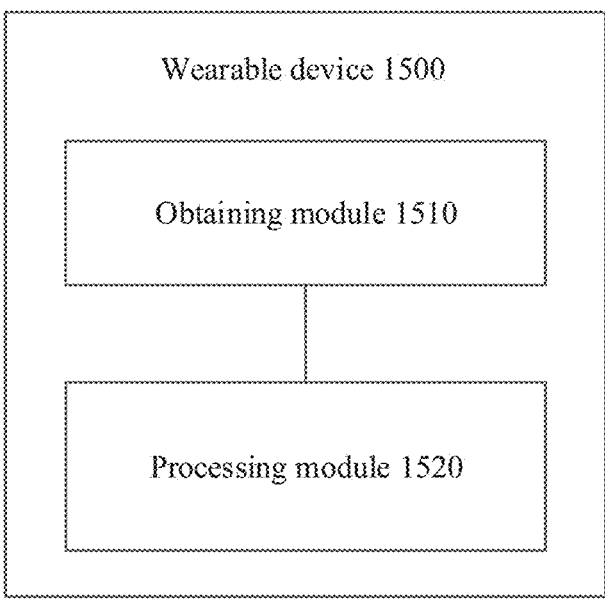
FIG. 15 is a schematic block diagram of a wearable device according to an embodiment of this application.

FIG. 15 is a schematic flowchart showing a wearable device 1500 according to an embodiment of this application. The wearable device 1500 includes an obtaining module 1510 and a processing module 1520. The wearable device 1500 may be configured to perform each of the foregoing methods. For example, the wearable device 1500 may be configured to perform at least one of the method 800, the method 900, the method 1000, and the method 1400 described above.

It is to be understood that the wearable device 1500 herein is embodied in a form of a functional module. The term "module" herein may be an application specific integrated circuit (ASIC), an electronic circuit, a processor (for example, a shared processor, a special purpose processor, or a group processor) configured to execute one or more software or firmware programs, a memory, a combinational logic circuit, and/or another suitable component that supports the described function. In an optional example, a person skilled in the art may understand that the wearable device 1500 may be specifically the wearable device in the foregoing method embodiments, or that the functions of the wearable device in the foregoing method embodiments may be integrated in the wearable device 1500. The wearable device 1500 may be configured to perform each process and/or step corresponding to the wearable device in the foregoing method embodiments. To avoid repetitions, details are not described herein again.

The foregoing wearable device 1500 has a function of implementing corresponding steps performed by the wearable device in the foregoing method embodiments. The foregoing function may be implemented by hardware, or may be implemented by hardware executing corresponding software. The hardware or software includes one or more modules corresponding to the foregoing functions.

In this embodiment of this application, the wearable device 1500 in FIG. 15 may alternatively be a chip or a chip system, for example, a system on chip (SoC).

Figure 16:
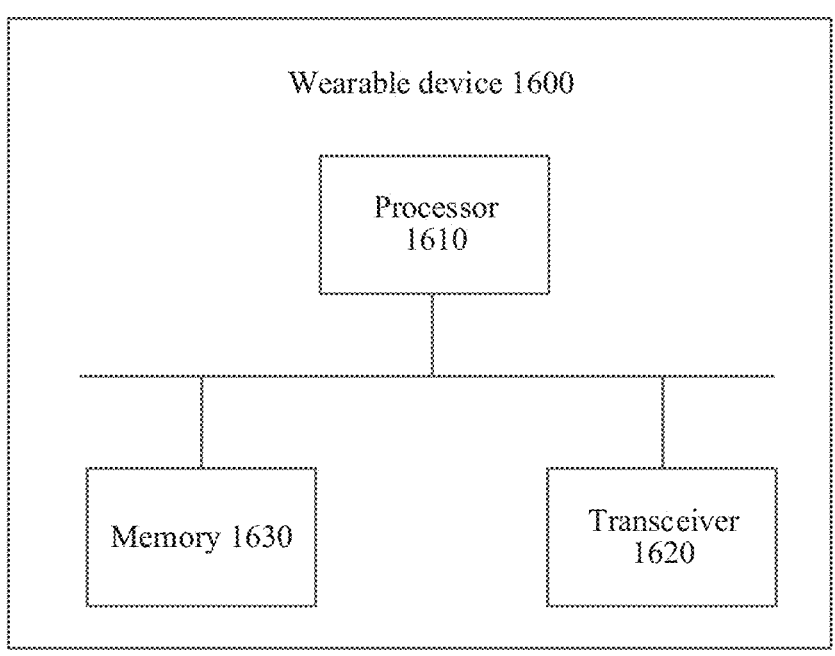
FIG. 16 is a schematic block diagram of another wearable device according to an embodiment of this application.

FIG. 16 is a schematic block diagram of another wearable device 1600 according to an embodiment of this application. The wearable device 1600 includes a processor 1610, a transceiver 1620, and a memory 1630. The processor 1610, the transceiver 1620, and the memory 1630 communicate with each other through an internal connection path, the memory 1630 is configured to store an instruction, and the processor 1620 is configured to execute the instruction stored in the memory 1630, to control the transceiver 1620 to send and/or receive a signal.

It is to be understood that the wearable device 1600 may be specifically the wearable device in the foregoing method embodiments, or the functions of the wearable device in the foregoing method embodiments may be integrated in the wearable device 1600. The wearable device 1600 may be configured to perform each step and/or process corresponding to the wearable device in the foregoing method embodiments. Optionally, the memory 1630 may include a read-only memory and a random access memory, and provide an instruction and data to the processor. A part of the memory may further include a non-volatile random access memory. For example, the memory may further store information about a device type. The processor 1610 may be configured to execute the instruction stored in the memory, and when the processor executes the instruction, the processor may perform each step and/or process corresponding to the wearable device in the foregoing method embodiment.

It is to be understood that in embodiments of this application, the processor 1610 may be a central processing unit (CPU). The processor may also be another general-purpose processor, a digital signal processor (DSP), an application-specific integrated circuit (ASIC), a field-programmable gate array (FPGA) or another programmable logic device, a discrete gate or transistor logic device, a discrete hardware component, or the like. The general-purpose processor may be a microprocessor, the processor may also be any conventional processor, or the like.

During implementation, the steps of the foregoing method may be completed through an integrated logic circuit of hardware or an instruction in the form of software in the processor. The steps of the method disclosed in combination with embodiments of this application may be directly performed by a hardware processor, or may be performed through a combination of hardware and software modules in the processor. A software module may be located in a mature storage medium in the art, such as a random access memory, a flash memory, a read-only memory, a programmable read-only memory, an electrically erasable programmable memory, or a register. The storage medium is located in the memory. The processor executes the instruction in the memory and performs the steps of the foregoing method in combination with hardware thereof. To avoid repetition, details are not described herein again.

This application further provides a computer-readable storage medium. The computer-readable storage medium is configured to store a computer program. The computer program is used to implement the method corresponding to the wearable device in the foregoing method embodiment.

This application also provides a chip system. The chip system is configured to support the wearable device in the foregoing method embodiment to implement the functions shown in embodiments of this application.

This application further provides a computer program product. The computer program product includes computer program code (which may also be referred to as code or an instruction). When the computer program code runs on a computer, the computer may perform the method corresponding to the wearable device shown in the foregoing method embodiment.

A person of ordinary skill in the art may be aware that, in combination with the examples described in embodiments disclosed in this specification, modules and algorithm steps can be implemented by electronic hardware or a combination of computer software and electronic hardware. Whether the functions are executed by hardware or software depends on specific applications and design constraint conditions of the technical solutions. A person skilled in the art may use different methods to implement the described functions for each particular application, but it is not to be considered that the implementation goes beyond the scope of this application.

It may be clearly understood by a person skilled in the art that, for the purpose of convenient and brief description, for a detailed operating process of the foregoing system, apparatus, and module, reference may be made to a corresponding process in the foregoing method embodiment. Details are not described herein again.

In the several embodiments provided in this application, it is to be understood that the disclosed system, apparatus, and method may be implemented in other manners. For example, the apparatus embodiments described above are merely exemplary. For example, division of modules is merely logical function division and may be other division manners during actual implementation. For example, a plurality of modules or components may be combined or integrated into another system, or some features may be omitted or not executed. In addition, the displayed or discussed mutual coupling or direct coupling or communication connection may be implemented by using some interfaces. The indirect coupling or communication connection between the apparatuses or modules may be electrical, mechanical, or in other forms.

The modules described as separate components may or may not be physically separated, and the components displayed as modules may or may not be physical modules, that is, may be located in one place or may be distributed on a plurality of network modules. Some or all of the modules may be selected according to actual needs to achieve the objectives of the solutions of embodiments.

In addition, functional modules in embodiments of this application may be integrated into one processing module, or the functional modules may exist alone physically, or two or more modules may be integrated into one module.

When the functions are implemented in the form of a software functional module and sold or used as an independent product, the functions may be stored in a computer-readable storage medium. Based on such an understanding, the technical solutions of this application essentially, or the part contributing to the prior art, or a part of the technical solutions may be implemented in the form of a software product. The computer software product is stored in a storage medium, and includes several instructions for enabling a computer device (which may be a personal computer, a server, a network device, or the like) to perform all or part of the steps of the method described in embodiments of this application. The foregoing storage medium includes: any medium that can store program code, such as a USB flash drive, a removable hard disk, a read-only memory (ROM), a random access memory (RAM), a magnetic disk, or a compact disc.

The foregoing descriptions are merely specific implementations of this application, but the protection scope of embodiments of this application is not limited thereto. Any variation or replacement readily figured out by a person skilled in the art within the technical scope disclosed in embodiments of this application shall fall within the protection scope of embodiments of this application. Therefore, the protection scope of embodiments of this application shall be subject to the protection scope of the claims.

The invention claimed is:

1. A wearable device, comprising:
a memory storing a computer program;
a processor coupled to a memory;
three pressure transducers (PTs); and
a photoplethysmography (PPG) sensor, wherein the PPG sensor comprises three light emitting diodes (LEDs) and one photo diode (PD), the one PD is located at a central position of the PPG sensor, and the three LEDs and the three PTs are all arranged around the PD in a circular array;
wherein the three PTs and the PPG sensor contact a wearer when the wearable device is in a worn state;

wherein the processor is configured to execute the computer program to cause the wearable device to perform operations comprising:

obtaining a plurality of pressure values collected by the three PTs;

obtaining a plurality of PPG signals collected by the PPG sensor; and determining a blood pressure value of the wearer based on the plurality of pressure values and the plurality of PPG signals;

wherein the plurality of pressure values are in one-to-one correspondence with the plurality of PPG signals, and a collection moment of each pressure value of the plurality of pressure values is same as that of a corresponding PPG signal of the plurality of PPG signals; and wherein the determining the blood pressure value of the wearer comprises:

respectively extracting waveform features of the plurality of PPG signals; and determining, based on a first PPG signal whose waveform feature amplitude is less than or equal to a preset waveform feature amplitude, a pressure value corresponding to the first PPG signal as a systolic blood pressure (SBP) in the blood pressure value of the wearer.

2. The wearable device according to claim 1, wherein the determining the blood pressure value of the wearer comprises:

inputting the plurality of pressure values and the waveform features of the plurality of PPG signals into a neural network model, wherein the neural network model is trained based on a historical pressure value and a waveform feature of a historical PPG signal, and is configured to measure blood pressure; and determining output of the neural network model as a diastolic blood pressure (DBP) in the blood pressure value of the wearer.

3. The wearable device according to claim 1, wherein before the obtaining the plurality of pressure values collected by the three PTs, the processor is further configured to execute the computer program to cause the wearable device to perform operations comprising:

outputting an operation guide, wherein the operation guide is configured to guide the wearer to apply a pressure perpendicular to a contact surface between the wearable device and human skin to the wearable device, and the operation guide comprises a pressure value required for the wearer to press.

4. The wearable device according to claim 3, wherein the processor is further configured to execute the computer program to cause the wearable device to perform operations comprising:

ending, during the pressure application by the wearer, blood pressure measurement based on at least one of the following conditions being satisfied:

an acceleration of the wearable device is greater than an acceleration threshold; and/or an angular velocity of the wearable device is greater than an angular velocity threshold.

5. The wearable device according to claim 3, wherein the processor is further configured to execute the computer program to cause the wearable device to perform operations comprising:

displaying a first interface, wherein a pressing position, prompt information, a pressure curve, and waveforms of the plurality of PPG signals are displayed on the first interface, the pressing position is a position where the wearer applies the pressure to the wearable device, the prompt information is used to prompt the wearer to apply the pressure to the wearable device based on the operation guide, and the pressure curve is the operation guide.

6. The method according to claim 5, wherein the pressing position comprises a first position and a second position of a screen of the wearable device, the first position is pressed by an index finger of the wearer, and the second position is pressed by a thumb of the wearer.

7. The wearable device according to claim 5, wherein the processor is further configured to execute the computer program to cause the wearable device to perform operations comprising:

displaying the blood pressure value on the first interface.

8. The wearable device according to claim 1, wherein before the obtaining the plurality of pressure values collected by the three PTs, the processor is further configured to execute the computer program to cause the wearable device to perform operations comprising:

detecting a triggering operation performed by the wearer on an automatic blood pressure measurement option; and determining, in response to the triggering operation performed by the wearer on the automatic blood pressure measurement option, whether a measurement time is reached;

wherein the obtaining the plurality of pressure values collected by the three PTs comprises:

obtaining the plurality of pressure values collected by the three PTs when the measurement time is reached.

9. The wearable device according to claim 8, wherein the determining the blood pressure value of the wearer comprises:

inputting, based on historical data comprising at least one pressure value of the plurality of pressure values, the plurality of pressure values, a waveform feature of a PPG signal corresponding to the at least one pressure value in the historical data, and waveform features of the plurality of PPG signals into a neural network model, to obtain the blood pressure value, wherein the historical data is used to represent measured data during historical blood pressure measurement, and the neural network model is trained based on a historical pressure value and a historical PPG signal and is configured for the blood pressure measurement.

10. The wearable device according to claim 8, wherein the determining the blood pressure value of the wearer comprises:

inputting, based on historical data not comprising a pressure value in the plurality of pressure values, the plurality of pressure values and waveform features of the plurality of PPG signals into a neural network model to obtain a temporary blood pressure value, wherein the historical data is used to represent measured data during historical blood pressure measurement; and determining the blood pressure value based on the temporary blood pressure value and a blood pressure value in the historical data.

11. The wearable device according to claim 1, wherein before the obtaining the plurality of pressure values collected by the three PTs, the processor is further configured to execute the computer program to cause the wearable device to perform operations comprising:

determining whether the wearable device satisfies a measurement condition;

wherein the obtaining the plurality of pressure values collected by the three PTs comprises:

obtaining the plurality of pressure values collected by the three PTs based on the measurement condition being satisfied.

12. The wearable device according to claim 11, wherein the measurement condition comprises at least one of the following:

an acceleration of the wearable device is less than or equal to an acceleration threshold, an initial pressure value is greater than or equal to a pressure threshold, an angular velocity of the wearable device is less than or equal to an angular velocity threshold, or an initial PPG signal satisfies a signal quality requirement, wherein the acceleration is used to represent a contact situation between the wearable device and the wearer, and the initial pressure value is used to represent a tightness for wearing the wearable device.

13. The wearable device according to claim 11, wherein the processor is further configured to execute the computer program to cause the wearable device to perform operations comprising:

prompting the wearer to wear the wearable device properly based on the measurement condition not being satisfied.

14. The method wearable device according to claim 2, wherein before the obtaining the plurality of pressure values collected by the three PTs, the processor is further configured to execute the computer program to cause the wearable device to perform operations comprising:

outputting an operation guide, wherein the operation guide is configured to guide the wearer to apply a pressure perpendicular to a contact surface between the wearable device and human skin to the wearable device, and the operation guide comprises a pressure value required for the wearer to press.

* * * * *